United States Patent
Kim et al.

(10) Patent No.: US 10,685,844 B2
(45) Date of Patent: Jun. 16, 2020

(54) HARDMASK COMPOSITION, METHOD OF FORMING PATTERN BY USING THE HARDMASK COMPOSITION, AND HARDMASK FORMED USING THE HARDMASK COMPOSITION

(71) Applicants: Samsung Electronics Co., Ltd., Suwon-si, Gyeonggi-do (KR); Research & Business Foundation SUNGKYUNKWAN UNIVERSITY, Suwon-si, Gyeonggi-do (KR)

(72) Inventors: Sangwon Kim, Seoul (KR); Changsik Song, Seoul (KR); Dongcheol Jeong, Suwon-si (KR); Minsu Seol, Seoul (KR); Hyeonjin Shin, Suwon-si (KR); Dongwook Lee, Suwon-si (KR); Taewoo Kim, Suwon-si (KR); Juhyen Lee, Suwon-si (KR); Hyejin Cho, Suwon-si (KR)

(73) Assignees: Samsung Electronics Co., Ltd., Gyeonggi-do (KR); Research & Business Foundation, Sungkyunkwan University, Gyeonggi-do (KR)

( * ) Notice: Subject to any disclaimer, the term of this patent is extended or adjusted under 35 U.S.C. 154(b) by 0 days.

(21) Appl. No.: 16/036,113

(22) Filed: Jul. 16, 2018

(65) Prior Publication Data
US 2019/0035635 A1    Jan. 31, 2019

(30) Foreign Application Priority Data
Jul. 27, 2017    (KR) .......................... 10-2017-0095711

(51) Int. Cl.
*H01L 21/308* (2006.01)
*H01L 29/16* (2006.01)
(Continued)

(52) U.S. Cl.
CPC .......... *H01L 21/3081* (2013.01); *C07B 37/12* (2013.01); *G03F 7/0043* (2013.01);
(Continued)

(58) Field of Classification Search
CPC ........................... H01L 21/3081; C07B 37/12
(Continued)

(56) References Cited

U.S. PATENT DOCUMENTS

| 4,550,015 A | 10/1985 | Korb et al. |
| 4,679,054 A | 7/1987 | Yoshikawa et al. |

(Continued)

FOREIGN PATENT DOCUMENTS

| CN | 102774824 A | 11/2012 |
| CN | 102775786 A | 11/2012 |

(Continued)

OTHER PUBLICATIONS

U.S. Appl. No. 15/332,287, filed Oct. 24, 2016.
(Continued)

*Primary Examiner* — Igwe U Anya
(74) *Attorney, Agent, or Firm* — Harness, Dickey & Pierce, P.L.C.

(57) ABSTRACT

Provided are a hardmask composition, a method of forming a pattern using the hardmask composition, and a hardmask formed using the hardmask composition. The hardmask composition includes a polar nonaqueous organic solvent and one of: i) a mixture of graphene quantum dots and at least one selected from a diene and a dienophile, ii) a Diels-Alder reaction product of the graphene quantum dots and the at least one selected from a diene and a dienophile, iii) a thermal treatment product of the Diels-Alder reaction product of graphene quantum dots and the at least one selected from a diene and a dienophile, or iv) a combination thereof.

20 Claims, 13 Drawing Sheets

(51) Int. Cl.

| | | |
|---|---|---|
| *C07B 37/12* | (2006.01) | |
| *G03F 7/004* | (2006.01) | |
| *H01L 21/311* | (2006.01) | |
| *G03F 7/16* | (2006.01) | |
| *G03F 7/027* | (2006.01) | |
| *H01L 21/033* | (2006.01) | |
| *G03F 7/09* | (2006.01) | |
| *C08L 101/02* | (2006.01) | |
| *B82Y 30/00* | (2011.01) | |
| *C07C 15/20* | (2006.01) | |
| *C07C 39/14* | (2006.01) | |
| *C07C 63/337* | (2006.01) | |
| *H01L 29/66* | (2006.01) | |

(52) U.S. Cl.
CPC ............. *G03F 7/027* (2013.01); *G03F 7/094* (2013.01); *G03F 7/168* (2013.01); *H01L 21/0332* (2013.01); *H01L 21/3086* (2013.01); *H01L 21/31144* (2013.01); *H01L 29/1606* (2013.01); *B82Y 30/00* (2013.01); *C07C 15/20* (2013.01); *C07C 39/14* (2013.01); *C07C 63/337* (2013.01); *C08L 101/02* (2013.01); *H01L 29/66575* (2013.01)

(58) Field of Classification Search
USPC ........................................................ 438/703
See application file for complete search history.

(56) References Cited

U.S. PATENT DOCUMENTS

| | | | |
|---|---|---|---|
| 5,328,560 | A | 7/1994 | Hanawa et al. |
| 5,432,227 | A | 7/1995 | Fujimura |
| 6,031,756 | A | 2/2000 | Gimzewski et al. |
| 6,120,858 | A | 9/2000 | Hirano et al. |
| 7,803,715 | B1 | 9/2010 | Haimson et al. |
| 8,008,095 | B2 | 8/2011 | Assefa et al. |
| 8,071,485 | B2 | 12/2011 | Lee et al. |
| 8,258,346 | B2 | 9/2012 | Rajendran |
| 8,524,594 | B2 | 9/2013 | Horikoshi |
| 8,871,639 | B2 | 10/2014 | Chien et al. |
| 8,999,529 | B2 | 4/2015 | Tetsuka et al. |
| 9,018,776 | B2 | 4/2015 | Song et al. |
| 9,105,780 | B2 | 8/2015 | Jeon et al. |
| 9,410,040 | B2 | 8/2016 | Li |
| 9,562,169 | B2 | 2/2017 | Wang et al. |
| 9,583,358 | B2 | 2/2017 | Kim et al. |
| 9,666,602 | B2 | 5/2017 | Lee et al. |
| 9,721,794 | B2 | 8/2017 | Shin et al. |
| 9,770,709 | B2 | 9/2017 | Swager et al. |
| 2003/0203314 | A1 | 10/2003 | Sebald et al. |
| 2005/0112383 | A1 | 5/2005 | Tanaka et al. |
| 2005/0238889 | A1 | 10/2005 | Iwamoto et al. |
| 2005/0250052 | A1 | 11/2005 | Nguyen |
| 2007/0026682 | A1 | 2/2007 | Hochberg et al. |
| 2007/0148557 | A1 | 6/2007 | Takei et al. |
| 2008/0032176 | A1 | 2/2008 | Shimizu et al. |
| 2008/0176741 | A1* | 7/2008 | Ma .................... B01J 21/185 502/182 |
| 2009/0011204 | A1 | 1/2009 | Wang et al. |
| 2009/0140350 | A1 | 6/2009 | Zhu |
| 2009/0297784 | A1 | 12/2009 | Xu et al. |
| 2010/0055464 | A1 | 3/2010 | Sung |
| 2010/0086463 | A1 | 4/2010 | Rudhard et al. |
| 2010/0170418 | A1* | 7/2010 | Afzali-Ardakani .... B82Y 30/00 106/287.2 |
| 2010/0218801 | A1 | 9/2010 | Sung et al. |
| 2010/0316950 | A1 | 12/2010 | Oguro et al. |
| 2011/0014111 | A1 | 1/2011 | Leugers et al. |
| 2011/0210282 | A1 | 9/2011 | Foley |
| 2011/0241072 | A1 | 10/2011 | Wang et al. |
| 2012/0153511 | A1 | 6/2012 | Song et al. |
| 2012/0181507 | A1 | 7/2012 | Dimitrakopoulos et al. |
| 2012/0193610 | A1 | 8/2012 | Kim |
| 2012/0279570 | A1 | 11/2012 | Li et al. |
| 2012/0326391 | A1* | 12/2012 | Hirose ................. F16J 15/022 277/312 |
| 2012/0329273 | A1* | 12/2012 | Bruce ............... H01L 21/02203 438/653 |
| 2013/0011630 | A1 | 1/2013 | Sullivan et al. |
| 2013/0119350 | A1 | 5/2013 | Dimitrakopoulos et al. |
| 2013/0133925 | A1 | 5/2013 | Kim et al. |
| 2013/0200424 | A1 | 8/2013 | An et al. |
| 2013/0203198 | A1 | 8/2013 | Min et al. |
| 2013/0236715 | A1 | 9/2013 | Zhamu et al. |
| 2013/0313523 | A1 | 11/2013 | Yun et al. |
| 2014/0015000 | A1 | 1/2014 | Nishiyama et al. |
| 2014/0098458 | A1 | 4/2014 | Almadhoun et al. |
| 2014/0102624 | A1* | 4/2014 | Melamed ................ B32B 25/16 156/154 |
| 2014/0183701 | A1 | 7/2014 | Choi et al. |
| 2014/0186777 | A1 | 7/2014 | Lee et al. |
| 2014/0187035 | A1 | 7/2014 | Posseme et al. |
| 2014/0239462 | A1 | 8/2014 | Shamma et al. |
| 2014/0299841 | A1 | 10/2014 | Nourbakhsh et al. |
| 2014/0320959 | A1 | 10/2014 | Jun et al. |
| 2014/0342273 | A1 | 11/2014 | Kim et al. |
| 2015/0001178 | A1 | 1/2015 | Song et al. |
| 2015/0004531 | A1 | 1/2015 | Choi et al. |
| 2015/0008212 | A1 | 1/2015 | Choi et al. |
| 2015/0023858 | A1 | 1/2015 | Tour et al. |
| 2015/0030968 | A1 | 1/2015 | Schwab et al. |
| 2015/0064904 | A1 | 3/2015 | Yao et al. |
| 2015/0129809 | A1 | 5/2015 | Gauthy et al. |
| 2015/0137077 | A1 | 5/2015 | Yun et al. |
| 2015/0200090 | A1 | 7/2015 | Chada et al. |
| 2015/0200091 | A1 | 7/2015 | Chada et al. |
| 2015/0348791 | A1 | 12/2015 | Higuchi et al. |
| 2015/0376014 | A1 | 12/2015 | Cesareo et al. |
| 2015/0377824 | A1 | 12/2015 | Ruhl et al. |
| 2016/0005625 | A1 | 1/2016 | Shin et al. |
| 2016/0011511 | A1 | 1/2016 | Shin et al. |
| 2016/0027645 | A1 | 1/2016 | Shin et al. |
| 2016/0043384 | A1 | 2/2016 | Zhamu et al. |
| 2016/0060121 | A1* | 3/2016 | Lee ...................... C01B 32/184 428/402 |
| 2016/0060122 | A1 | 3/2016 | Tour et al. |
| 2016/0130151 | A1 | 5/2016 | Kurungot et al. |
| 2016/0152477 | A1* | 6/2016 | Xiao ...................... C07B 37/12 252/502 |
| 2016/0152748 | A1 | 6/2016 | Goffredi et al. |
| 2016/0179005 | A1 | 6/2016 | Shamma et al. |
| 2016/0211142 | A1 | 7/2016 | Kim et al. |
| 2016/0225991 | A1 | 8/2016 | Schwab et al. |
| 2016/0240841 | A1 | 8/2016 | He et al. |
| 2016/0282721 | A1* | 9/2016 | Seol ........................ G03F 7/094 |
| 2016/0284811 | A1 | 9/2016 | Yu et al. |
| 2016/0291472 | A1 | 10/2016 | Shin et al. |
| 2016/0308134 | A1 | 10/2016 | Li et al. |
| 2016/0346769 | A1 | 12/2016 | Kim et al. |
| 2016/0369149 | A1 | 12/2016 | Liu et al. |
| 2017/0368535 | A1 | 12/2017 | Chopra et al. |
| 2018/0022994 | A1 | 1/2018 | Isaji et al. |
| 2018/0047906 | A1 | 2/2018 | Begue et al. |
| 2018/0251678 | A1 | 9/2018 | Saikia et al. |
| 2019/0031906 | A1* | 1/2019 | Kim ....................... C09D 165/00 |
| 2019/0101524 | A1 | 4/2019 | Han et al. |
| 2019/0294047 | A1 | 9/2019 | Shin et al. |

FOREIGN PATENT DOCUMENTS

| | | |
|---|---|---|
| EP | 1703328 A1 | 9/2006 |
| EP | 2 735 904 A1 | 5/2014 |
| EP | 2950334 A1 | 12/2015 |
| EP | 3 076 239 A1 | 10/2016 |
| JP | H 5-343308 A | 12/1993 |
| JP | 3396846 B2 | 4/2003 |
| JP | 2005-173552 A | 6/2005 |
| JP | 4488234 B2 | 6/2010 |
| JP | 4531400 B2 | 8/2010 |
| JP | 2013-006732 A | 1/2013 |

(56) References Cited

FOREIGN PATENT DOCUMENTS

| | | |
|---|---|---|
| JP | 2013-185155 A | 9/2013 |
| JP | 2013-208881 A | 10/2013 |
| JP | 2017-036411 A | 2/2017 |
| JP | 2017064714 A | 4/2017 |
| KR | 10-105721 B1 | 8/2011 |
| KR | 10-2012-0024756 | 3/2012 |
| KR | 10-1257694 B1 | 4/2013 |
| KR | 11262515 B1 | 5/2013 |
| KR | 10-2013-0132103 A | 12/2013 |
| KR | 10-1343014 B1 | 12/2013 |
| KR | 10-2014-0066524 A | 6/2014 |
| KR | 10-142317 B1 | 7/2014 |
| KR | 10-1439030 B1 | 9/2014 |
| KR | 10-2015-0047326 A | 5/2015 |
| KR | 10-2016-0012804 A | 2/2016 |
| KR | 20160100172 A | 8/2016 |
| KR | 10-2016-0118782 A | 10/2016 |
| WO | WO-2013/100365 A1 | 7/2013 |
| WO | WO-2014/135455 A1 | 9/2014 |

OTHER PUBLICATIONS

U.S. Appl. No. 14/791,912, filed Jul. 6, 2016.
Notice of Allowance and Fee(s) Due for U.S. Appl. No. 15/332,287 dated Aug. 9, 2018.
Office Action for U.S. Appl. No. 14/791,912 dated Aug. 10, 2018.
U.S. Office Action dated Mar. 15, 2019 issued in U.S. Appl. No. 15/925,034.
Morozan, A. et al., "Catalytic activity of cobalt and iron phthalocyanines or porphyrins supported on different carbon nanotubes towards oxyen reduction reaction," CARBON, vol. 49, No. 14, Jul. 2, 2011, pp. 4839-4847.
Ghani, F. et al., "Solubility Properties of Unsubstituted Metal Phthalocyanines in Different Types of Solvents," Journal of Chemical and Engineering Data, vol. 57, No. 2, Jan. 27, 2012, pp. 439-449.
Li, Z. et al., "Superstrutured Assembly of Nanocarbons: Fullerenes, Nanotubes, and Graphene," Chemical Reviews, vol. 115, No. 15, Jul. 13, 2015, pp. 7046-7117.
Extended European Search Report for EP Appl. No. 18183070.4 dated Nov. 23, 2018.
U.S. Appl. No. 15/944,920, filed Apr. 4, 2018.
U.S. Appl. No. 15/925,034, filed Mar. 9, 2018.
S. Sarkar et al., 'Diels-Alder Chemistry or Graphite and Graphene: Graphene as Diene and Dienophile' *Journal of the American Chemistry Society*, vol. 133, Feb. 2011, pp. 3324-3327.
Office Action dated Sep. 3, 2019, issued in corresponding U.S. Appl. No. 15/925,034.
Office Action dated Jan. 2, 2020, issued in co-pending U.S. Appl. No. 15/925,034.
U.S. Office Action dated May 10,2016 issued in co-pending U.S. Appl. No. 14/791,912.
U.S. Office Action dated March 28, 2016 issued in co-pending U.S. Appl. No. 14/697,150.
Silane Coupling Agents, Xiameter for Dow Corning, Silicones Simplified, pp. 1-7, (2009).
Grenadier, et al. "Dry etching techniques for active devices based on hexagonal boron nitride epilavers," Journal of Vacuum Science & Technology A, Vol. 31. pp. 061517-061517.3 (2013).
S. Hascik, et al. "Dry etching of carbon layers in various etch gases," Vacuum, vol. 58. pp. 434-439 (2000).
Albert S. Nazarov, et al. "Functionalization and dispersion of h-BN nanosheets treated with Lngmanic reagents," Chemistry, An Asian Journal, vol. 7, Issue 3, pp. 1-6. (2012).
U.S. Office Action dated Aug. 16, 2016 issued in co-pending U.S. Appl. No. 14/697,150.
U.S. Office Action dated September 30, 2016 issued in co-pending U.S. Appl. No. 14/691,150.
European Search Report dated September 30, 2015 issued in European Application No. 15169702.6.
Zhang, et al. "Fabrication of highly oriented reduced graphene oxide microbelts array for massive production of sensitive ammonia gas sensors". Journal of MicroMechanics and MicroEngineering, vol. 23, pp. 1-8. (2013).
Huang, et al. "An innovative way of etching MoS2: Characterization and mechanistic investigation," Nano Research. vol. 6, No. 3. pp. 200-207 (2013).
Hwang, et al. "Transparent actuator made with few layer graphene electrode and dielectric elastomer, for variable focus lens", Applied Physics Letters, vol. 103, pp. 023106-1-023106-5. (2013).
U.S. Notice of Allowance dated July 16, 2018 issued in copending U.S. Appl. No. 14/825,792.
U.S. Notice of Allowance dated July 20. 2018 issued in copending U.S. Appl. No. 15/611,935.
U.S. Office Action dated May 22, 2013 issued in U.S. Appl. No. 14/843,003.
U.S. Office Action dated Feb. 22. 2018 issued in U.S. Appl. No. 14/825,792.
U.S. Notice of Allowance dated Mar. 27, 2018 issued in U.S. Appl. No. 15/611,935.
U.S. Office Action dated Dec. 5, 2017 issued in U.S. Appl. No. 15/611,935.
U.S. Notice of Allowance dated Feb. 1, 2018 issued in U.S. Appl. No. 14/791,912.
U.S. Office Action dated Jun. 13, 2017 issued in U.S. Appl. No. 14/791,912.
U.S. Office Action dated Feb. 8, 2017 issued U.S. Appl. No. 14/791,912.
U.S. Office Action dated Oct. 6, 2017 issued U.S. Appl. No. 14/843,003.
U.S. Notice of Allowance dated Aug. 28, 2017 issued U.S. Appl. No. 14/791,912.
U.S. Notice of Allowance dated Oct. 19, 2016 issued in U.S. Appl. No. 14/725,390.
U.S. Office Action dated Mar. 22, 2016 issued in U.S. Appl. No. 14/725,390.
U.S. Notice of Allowance dated Mar. 15, 2017 issued in U.S. Appl. No. 14/697,150.
Shin, et al. "Mass Production of Graphene Quantum Dots by One-Pot Synthesis Directly from Graphite in High Yield," small communications, vol. 10, No. 5, pp. 866-870 (2014).
Wang, et al. "Gram-scale synthesis of single-crystalline graphene quantum dots with superior optical properties," Nature Communications, pp. 1-9 (2014).
Song, et al. "Highly Efficient Light-Emitting Diode of Graphene Quantum Dots Fabricated from Graphite Intercalation Compounds," Adv. Optical Mater, pp. 1-8 (2014).
Extended European Search Report dated Aug. 17, 2016 issued in European Application No. 15193939.4.

\* cited by examiner

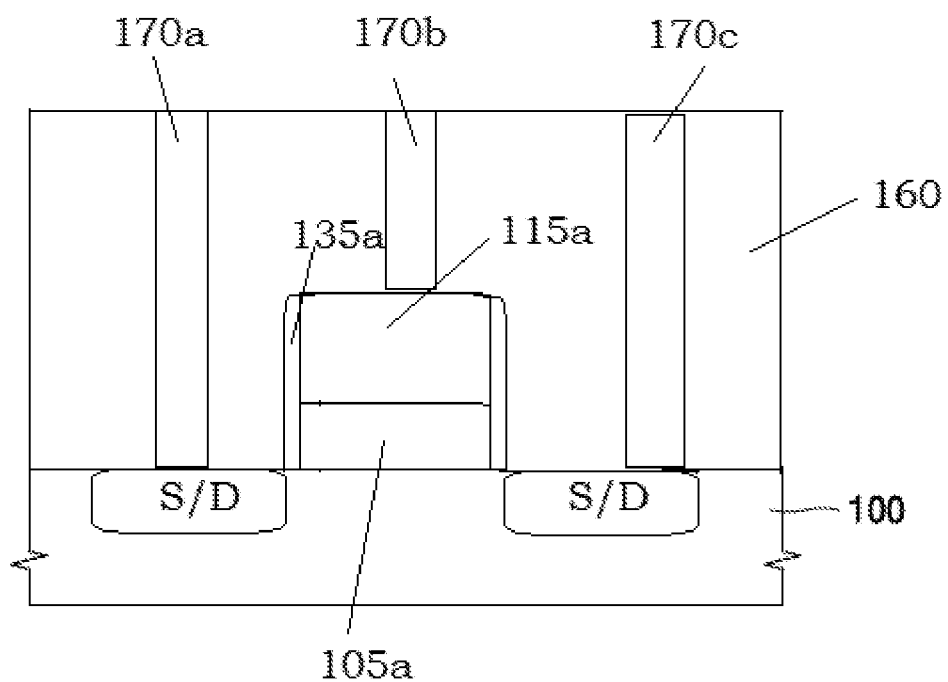

HARDMASK COMPOSITION, METHOD OF FORMING PATTERN BY USING THE HARDMASK COMPOSITION, AND HARDMASK FORMED USING THE HARDMASK COMPOSITION

CROSS-REFERENCE TO RELATED APPLICATION

This application claims the benefit of Korean Patent Application No. 10-2017-0095711, filed on Jul. 27, 2017, in the Korean Intellectual Property Office, the disclosure of which is incorporated herein in its entirety by reference.

BACKGROUND

1. Field

The present disclosure relates to a hardmask composition, a method of forming a pattern by using the hardmask composition, and a hardmask formed using the hardmask composition.

2. Description of Related Art

The semiconductor industry has developed an ultrafine technique for providing a pattern of several to several tens of nanometers in size. Such an ultrafine technique benefits from effective lithographic techniques. A typical lithographic technique includes forming a material layer on a semiconductor substrate, coating a photoresist layer on the material layer, exposing and developing the same to obtain a photoresist pattern, and etching the material layer by using the photoresist pattern as a mask.

As a size of a pattern to be formed becomes smaller, it has become difficult to form a fine pattern having a desirable profile by using a typical lithographic technique alone. In this regard, a layer called a "hardmask" may be formed between a material layer to be etched and a photoresist layer and used to form a fine pattern. The hardmask serves as an interlayer that transfers the fine photoresist pattern to the material layer through a selective etching process. Thus, the hardmask layer needs to have chemical resistance, thermal resistance, and etching resistance in order to be durable against various etching processes.

As semiconductor devices have become highly integrated, an aspect ratio of a material layer has increased as a line width of the material layer has narrowed, while its height has been maintained the same or has relatively increased. Under these circumstances, the heights of a photoresist layer and a hardmask pattern need to be increased for etching. However, there is a limitation in increasing the heights of the photoresist layer and the hardmask pattern. In addition, the hardmask pattern may be damaged during an etching process performed to obtain a material layer having a narrow line width, thus deteriorating electrical characteristics of devices.

In this regard, methods of using a hardmask in the form of a single layer or a stack of multiple layers formed of a conductive or insulating material, such as a polysilicon layer, a tungsten layer, and a nitride layer, have been suggested. However, since the single layer or the multiple layers are formed at a high deposition temperature, modification of modification of physical properties of the material layer may occur. Therefore, new hardmask materials are being developed.

SUMMARY

Provided is a hardmask composition having improved solubility characteristics in a semiconductor process solvent and improved etching resistance.

Provided is a method of forming a pattern by using the hardmask composition.

Provided is a hardmask formed using the hardmask composition.

Additional aspects will be set forth in part in the description which follows and, in part, will be apparent from the description, or may be learned by practice of the presented embodiments.

According to some embodiments, a hardmask composition includes one of i) a mixture of graphene quantum dots and at least one selected from a diene and a dienophile, ii) a Diels-Alder reaction product of the graphene quantum dots and the at least one selected from a diene and a dienophile, iii) a thermal treatment product of the Diels-Alder reaction product of the graphene quantum dots and the at least one selected from a diene and a dienophile, or iv) a combination thereof; and a polar nonaqueous organic solvent.

According to some embodiments, a method of forming a pattern includes forming a target etching layer on a substrate, forming a hardmask on the target etching layer, forming a photoresist layer on the hardmask, forming a hardmask pattern using the photoresist layer as an etch mask, and etching the target layer using the hardmask pattern as an etch mask. The hardmask includes a product of coating the above-described hardmask composition onto the target etching layer and thermally treating the hardmask composition. The hardmask pattern includes the product of coating and thermally treating the hardmask composition.

According to some embodiments, a hardmask includes a product resulting from coating and thermally treating the above-described hardmask composition.

In some embodiments, the product resulting from coating and thermally treating the hardmask composition may be the thermal treatment product of the Diels-Alder reaction production of the graphene quantum dots and the at least one selected from a diene and a dienophile.

In some embodiments, an oxygen content in the graphene quantum dots in the hardmask may be about 3% or more lower than an oxygen content in the graphene quantum dots as a starting material, as analyzed by X-ray photoelectron spectroscopy.

In some embodiments, the hardmask may have a reduced intensity of a peak corresponding to free hydroxyl groups at a wave number of about 2700 cm-1 to 3200 cm-1, relative to a peak corresponding to free hydroxyl groups in the graphene quantum dots used as a starting material; and an increased mixed ratio of $sp^3$ carbon to sp2 carbon, relative to a corresponding peak of the graphene quantum dots used as a starting material, as analyzed by infrared (IR) spectroscopy.

BRIEF DESCRIPTION OF THE DRAWINGS

These and/or other aspects will become apparent and more readily appreciated from the following description of the embodiments, taken in conjunction with the accompanying drawings in which:

FIGS. 7A to 7E are cross-sectional views for explaining a method of forming an electronic device using a hardmask composition according to some example embodiments.

DETAILED DESCRIPTION

Figure 1:
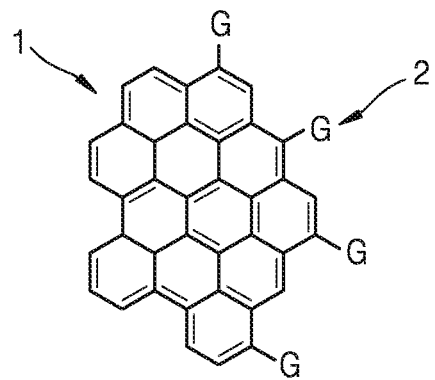
FIG. 1 is a schematic illustration of graphene quantum dots (GQDs) according to some embodiments of inventive concepts.

Reference will now be made in detail to some example embodiments, which are illustrated in the accompanying drawings, wherein like reference numerals refer to like elements throughout. In this regard, example embodiments may have different forms and should not be construed as being limited to the descriptions set forth herein. Accordingly, the embodiments are merely described below, by referring to the figures, to explain aspects. As used herein, the term "and/or" includes any and all combinations of one or more of the associated listed items. Expressions such as "at least one of," when preceding a list of elements, modify the entire list of elements and do not modify the individual elements of the list.

Hereinafter, some example embodiments of a hardmask composition, a method of forming a pattern using the hardmask composition, and a hardmask formed from the hardmask composition will be described in detail.

According to some example embodiments of inventive concepts, a hardmask composition includes: i) a mixture of graphene quantum dots and at least one selected from diene and dienophile, ii) a Diels-Alder reaction product of graphene quantum dots and at least one selected from a diene and a dienophile, iii) a thermal treatment product of the Diels-Alder reaction product of graphene quantum dots and at least one selected from a diene and a dienophile, or iv) a mixture thereof; and a polar nonaqueous organic solvent.

In the hardmask composition, according to some embodiments, the graphene quantum dots may have at an end thereof at least one first functional group selected from the group consisting of a hydroxyl group, a carbonyl group, a carboxyl group, an epoxy group, and an amine group. When such a first functional group is bound to the edge of the graphene quantum dots, a hardmask formed from the hardmask composition may have improved etching resistance, relative to when such first functional groups are present both at the end and center of the graphene quantum dots relative to when such first functional groups are present at the center of the graphene quantum dots.

The amount of the graphene quantum dots may be in a range of about 0.1 wt % to about 40 wt % based on a total weight of the hardmask composition. When the amount of the graphene quantum dots is within this range, a hardmask formed from the hardmask composition may have improved stability and improved etching resistance.

In the hardmask composition, according to some embodiments, the diene and the dienophile may have, for example, a second functional group which is the same as or similar to that of the polar nonaqueous organic solvent. Accordingly, the Diels-Alder reaction product of graphene quantum dots and at least one selected from the diene and the dienophile may include the second functional group that imparts solubility in the polar nonaqueous organic solvent. Thus, the hardmask composition according to one or more embodiments may have improved solubility characteristics and improved dispersion characteristics in a variety of semiconductor process solvents, compared to a hardmask composition using graphene quantum dots used just as a starting material.

As used herein, the term "second functional group" may be construed as a moiety not only the above-described functional group.

As used herein, the term "semiconductor process solvent" may refer to a solvent used in forming a semiconductor layer pattern, for example, a hardmask pattern. The semiconductor process solvent may refer to a polar nonaqueous organic solvent used in the hardmask composition according to embodiments.

When a common graphene is used in a hardmask composition, the graphene have a limitation due to its low solubility in a process solvent used in forming a hardmask. In this regard, inventive concepts relate to introducing into graphene quantum dots a functional group able to improve solubility characteristics in a process solvent and using the graphene quantum dots having the functional group in forming a hardmask. The functional group able to improve the solubility characteristics in a process solvent as described above may be easily removed through thermal treatment. The thermal treatment may be performed at a temperature of, for example, about 400° C. or less, for example, about 200° C. or less, or about 100° C. to about 160° C.

In the hardmask composition, according to some embodiments, by introducing a second functional group that may be easily removed from the graphene quantum dots by a post-treatment (for example, thermal treatment) through a simple organic reaction, the hardmask may have improved solubility characteristics in a process solvent, improved solution stability, and improved etching selectivity.

The second functional group may be at least one divalent group selected from, for example, a C1-C20 alkenylene group having at least one carboxyl group, an organic group (for example, a C1-C20 alkenyl group having a carbonyl group) having at least one carbonyl group, an organic group having at least one —COOR (wherein R may be a C1-C20 alkyl group or a C2-C20 alkenyl group), a hydrogenated C1-C10 cyanoalkylene group, a hydrogenated C4-C20 heterocyclic group, a hydrogenated C2-C20 alkenyl group, and a hydrogenated C4-C20 condensed arylene group.

In some embodiments, the graphene quantum dots may include a plurality of second functional groups as described above.

The graphene quantum dots having the first functional group or the second functional group as described above may be removed under thermal treatment conditions. The graphene quantum dots from which the second functional group is removed may have less functional groups, for example, free hydroxyl groups, at an edge thereof, relative to graphene quantum dots used as a starting material. This is attributed to that hydroxyl groups present at the edge of the graphene quantum dots are partially involved in the reaction with a diene or a dienophile. The reduced number of free hydroxyl groups in the reaction product constituting a hardmask according to some embodiments, the reaction product resulting from thermally treating a Diels-Alder reaction product of the graphene quantum dots and at least one selected from diene and dienophile, relative to graphene quantum dots used as a starting material, may be identified from a reduced intensity of peaks associated with free hydroxyl groups (for example, at a wave number of about 2700 $cm^{-1}$ to about 3200 $cm^{-1}$) in the infrared spectra.

In some embodiments, the hardmask according to one or more embodiments may have a reduced intensity of a peak corresponding to free hydroxyl groups (at a wave number of about 2700 $cm^{-1}$ to about 3200 $cm^{-1}$) in the IR spectra, relative to a peak corresponding to free hydroxyl group in graphene quantum dots used as a starting material. The hardmask according to one or more embodiments may have an increased mixed ratio of $sp^3$ carbon to $sp^2$ carbon, relative to a corresponding peak of graphene quantum dots used as a starting material referring to information from a peak at a wave number of about 750 $cm^{-1}$ to about 1000 $cm^{-1}$.

In the mask composition according to embodiments, the thermal treatment product of the graphene quantum dots having a second functional group as described above may have different structural characteristics from graphene quantum dots used as a starting material. This may be identified based on the shape of a peak at about 282 eV to about 286 eV in the X-ray photoelectron spectra (XPS), the peak giving information about a mixed ratio of $sp^3$ carbon to $sp^2$ carbon.

In the hardmask according to embodiments, the thermal treatment product of a Diels-Alder reaction product of the graphene quantum dots and at least one selected from diene and dienophile may have a reduced oxygen content by about 3% or greater, for example, about 4% or greater, relative to an oxygen content of graphene quantum dots used as a starting material, as analyzed by XPS. For example, when an oxygen content of graphene quantum dots used as a starting material is about 18.2 atom %, the final product constituting the hardmask, i.e., the thermal treatment product of a Diels-Alder reaction product of the graphene quantum dots and at least one selected from diene and dienophile may have an oxygen content of about 17.4 atom %, which is about 4.37% lower than the oxygen content of the starting material.

In the hardmask according to embodiments, the hardmask may have an increased peak intensity ratio ($I_{sp3}/I_{sp2}$) of $sp^3$ carbon peak to $sp^2$ carbon peak, relative to a peak intensity ratio ($I_{sp3}/I_{sp2}$) of $sp^3$ carbon peak to $sp^2$ carbon peak in the graphene quantum dots used as a starting material, as analyzed by X-ray photoelectron spectroscopy (XPS).

In some embodiments, the amount of the second functional group introduced into the graphene quantum dots (FGQD) to impart solubility in the polar nonaqueous organic solvent used as a process solvent may be identified by thermogravimetric analysis (TGA) of the graphene quantum dots (FGQD) having the second functional group and the graphene quantum dots (GQD) used as a starting material. For example, the graphene quantum dots (FGQD) may have a weight loss of about 24 wt % to about 34 wt % at a temperature of about 300° C. to about 600° C., relative to the graphene quantum dots (GQD). This weight loss is attributed to the second functional group bound to the graphene quantum dots (GQD) and FGQD.

For example, the polar nonaqueous organic solvent may be at least one selected from propylene glycol monomethyl ether acetate (PGMEA), propylene glycol monomethyl ether (PGME), cyclohexanone, and ethyl lactate.

As used herein, the term "graphene quantum dots" may be defined as follows.

Graphene quantum dots ("GQD") may refer to graphene in the form of dots or sheets having a size of about 1 nm to about 50 nm, for example, about 1 nm to about 30 nm, or about 1 nm to about 10 nm, made semi-conductive from conductive graphene. For example, the graphene quantum dots may refer to oxidized graphene quantum dots and/or a reduced product of oxidize graphene quantum dots having a size of about 1 nm to about 10 nm.

When the graphene quantum dots have a size within this range, an etch rate of the hardmask may be appropriately controlled, and the graphene quantum dots may have improved dispersion characteristics in the mask composition.

The term "size" of the graphene quantum dots may refer to an average particle diameter when the graphene quantum dots are spherical (or dot form), may refer to a diameter on a 2-dimensional plane when the graphene quantum dots have a planar structure, may refer to a length of the major axis when the graphene quantum dots are in elliptical or sheet form. The graphene quantum dots may have a 2-dimensional planar structure or a spherical structure. Herein, the term "spherical" may mean all types of shape substantially close to a sphere, for example, a spherical or elliptical shape.

The graphene quantum dots may have, for example, a size of about 1 nm to about 10 nm, for example, about 5 nm to about 8 nm, or about 6 nm to about 8 nm, and may include, for example, 300 layers or less, for example, 100 layers or less, or about 1 layer to about 20 layers. The graphene quantum dots may have a thickness of about 100 nm or less.

The graphene quantum dots may have a 2-dimensional sheet form with a size to thickness ratio of about 3 to about 30, for example, about 5 to about 25.

When the graphene quantum dots are in the form of a sheet, the size (a length of the major axis) may be about 10 nm or less, and a length of the minor axis may be about 0.5 nm to about 5 nm. When a size, the number of layers, and a thickness of the graphene quantum dots are within these ranges, the hardmask composition may have improved stability.

For example, the graphene quantum dots may include about 100 to about 60,000 conjugated atoms, and in some embodiments, about 100 to about 600 conjugated atoms. The graphene quantum dots may have the dual nature as a diene and a dienophile as represented in Reaction Scheme 1.

[Reaction Scheme 1]

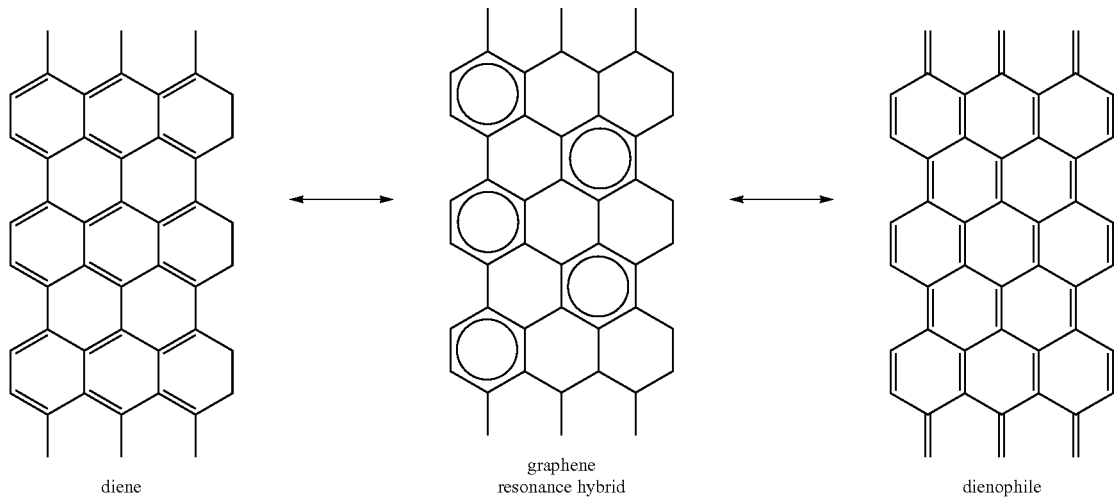

diene      graphene resonance hybrid      dienophile

In the term "graphene quantum dots" used herein, "graphene" may refer to a sheet structure of a single atomic layer formed by a carbon nanostructure that forms polycyclic aromatic molecules in which a plurality of carbon atoms are covalently bound and aligned in a planar shape; a network structure in which a plurality of carbon nanostructures as a small film having a plate shape are interconnected and aligned in a planar shape; or a combination thereof. The covalently bound carbon atoms may form 6-membered rings as repeating units, but may further include 5-membered rings and/or 7-membered rings. The graphene may be formed by stacking a plurality of layers including several sheet structures and/or network structures. For example, the graphene quantum dots may have an average thickness of about 100 nm or less, and in some embodiments, about 10 nm or less, and in some other embodiments about 0.01 nm to about 10 nm. The graphene quantum dots may have a first functional group at an edge thereof.

As used herein, the term "Diels-Alder reaction product of graphene quantum dots and at least one selected from diene and dienophile" may refer to a product resulting from the Diels-Alder reaction between the graphene quantum dots and at least one selected from diene and dienophile.

The Diels-Alder reaction is a reaction between diene as a nucleophile and dienophile as an electrophile under an acid or heat condition to generate a ring having two sigma ($\sigma$) bonds and one pie ($\pi$) bond through a single-stage reaction (Reaction Scheme 2).

[Reaction Scheme 2]

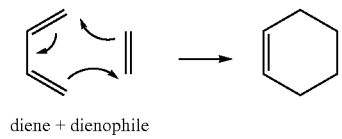

diene + dienophile

The temperature of the Diels-Alder reaction may vary depending to types of diene and dienophile, or the like. For example, the Diels-Alder reaction may be performed at a temperature of about 25° C. to about 120° C., and in some embodiments, about 25° C., about 50° C., about 70° C., or about 120° C.

In some embodiments, the Diels-Alder reaction may be performed without a solvent or in the presence of a solvent according to types of the diene and dienophile. The solvent may be any solvent which may dissolve or disperse the diene and the dienophile. In some other embodiments, the Diels-Alder reaction may be performed in the presence of an oxidizing agent. The oxidizing agent may be any oxidizing agent available in the art. In the hardmask composition, according to some embodiments, the graphene quantum dots used to prepare the hardmask composition may have at an edge thereof at least one first functional group G (denoted by reference numeral 2) selected from the group consisting of a hydroxyl group, a carbonyl group, a carboxyl group, an epoxy group, an amine group, as illustrated in FIG. 1. In FIG. 1, reference numeral 1 denotes the graphene quantum dots.

The COOH-functionalized GQDs may be obtained by adding chloroacetic acid to bare GQDs or OH-functionalized GQDs. The OH-functionalized GQDs may be obtained by a general method of introducing a hydroxyl group to GQDs. For example, the OH-functionalized GQDs may be obtained by grinding GQDs into a certain size, adding a base and an oxidizing agent to the ground GQDs, and then further grinding a resulting product. An example of the base may be sodium hydroxide. An example of the oxidizing agent may be hydrogen peroxide.

During the Diels-Alder reaction of the graphene quantum dots 1 of FIG. 1 and at least one selected from diene and dienophile, the graphene quantum dots 1 may be bound to a second functional group that is the same as or similar to a functional group in the polar nonaqueous organic solvent as a semiconductor process solvent. For example, the second functional group may be at least one) divalent group selected from, for example, a C2-C20 alkenylene group having at least one carboxyl group, an organic group (for example, a C2-C20 alkenyl group having a carbonyl group) having at least one carbonyl group, an organic group having at least one —COOR (wherein R may be a C1-C20 alkyl group or a C2-C20 alkenyl group), a hydrogenated C1-C10 cyanoalkylene group, a hydrogenated C4-C20 heterocyclic group, a hydrogenated C1-C20 alkenyl group, and a hydrogenated C4-C20 condensed arylene group.

In some embodiments, the amount of the at least one selected from diene and dienophile may be about 100 parts by weight or higher, for example, about 100 parts to about 500 parts by weight, based on 100 parts by weight of the graphene quantum dots. When the amount of the at least one selected from diene and dienophile is within this range, the Diels-Alder reaction product of the graphene quantum dots as the dienophile and the diene may have improved solubility characteristics, so that formation of a hardmask layer may be facilitated.

Reaction Scheme 3 illustrates a Diels-Alder reaction of graphene quantum dots with tetracyanoethylene or maleic anhydride as a dienophile. In Reaction Scheme 3, for convenience of illustration, the first functional group of the graphene quantum dots is omitted, and only the second functional group is shown.

[Reaction Scheme 3]

(a)

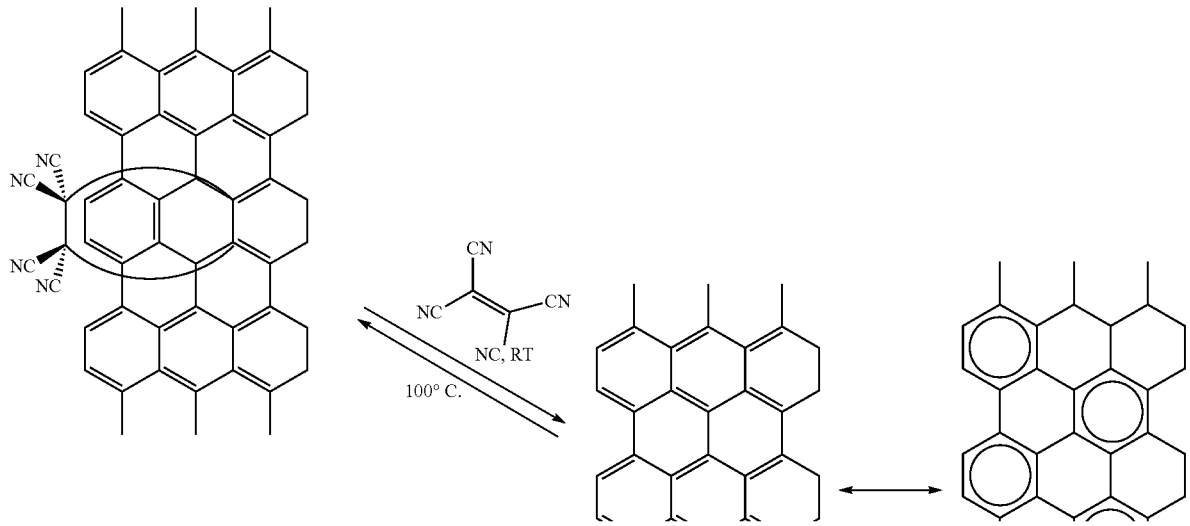

(b)

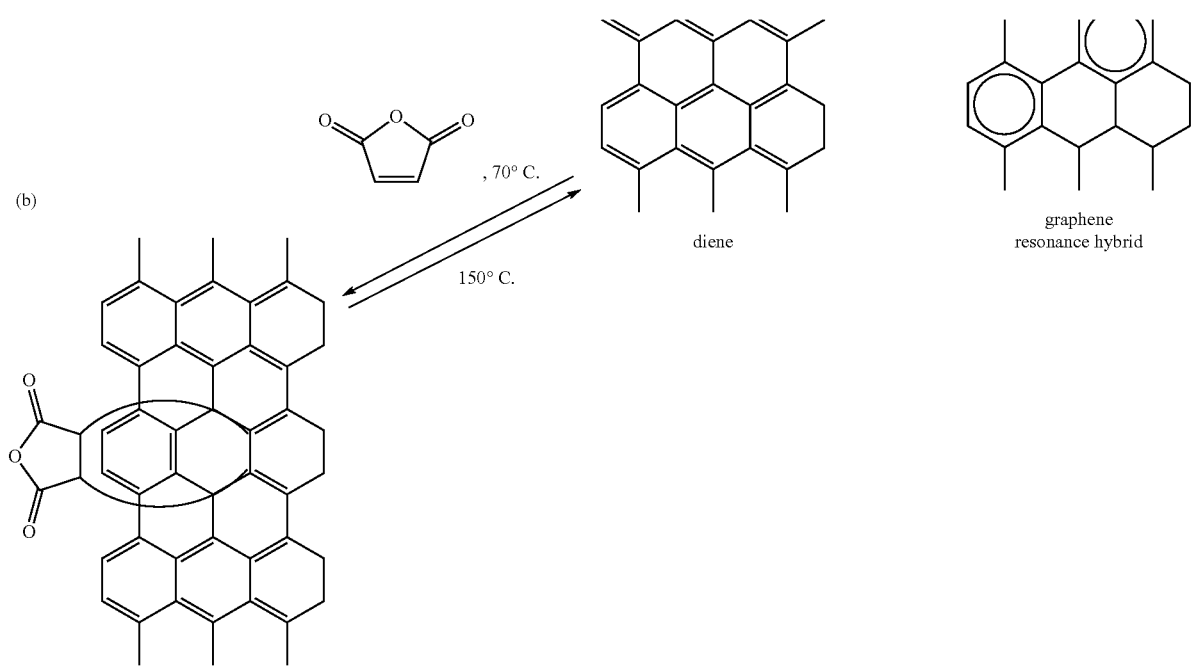

Referring to Reaction Scheme 3, the graphene quantum dots serving as a diene may form a compound (a) represented by Formula 5 or a compound (b) represented by Formula 6.

Reaction Scheme 4 illustrates a Diels-Alder reaction of graphene quantum dots with a compound of Formula 1 or a compound of Formula 2 as a diene. In Reaction Scheme 3, for convenience of illustration, the first functional group of the graphene quantum dots is omitted, and only the second functional group is shown.

dienophile. Referring to Reaction Schemes 3 and 4, in the Diels-Alder reaction product of the graphene quantum dots and the diene and/or the Diels-Alder reaction product of the graphene quantum dots and the dienophile, the second functional group derived from the dienophile and the diene bound to the graphene quantum dots may be removed when the temperature is controlled to about 100° C., about 150° C., or about 160° C.

The at least one selected from dienophile and diene may be, for example, at least one selected from the group

[Reaction Scheme 4]

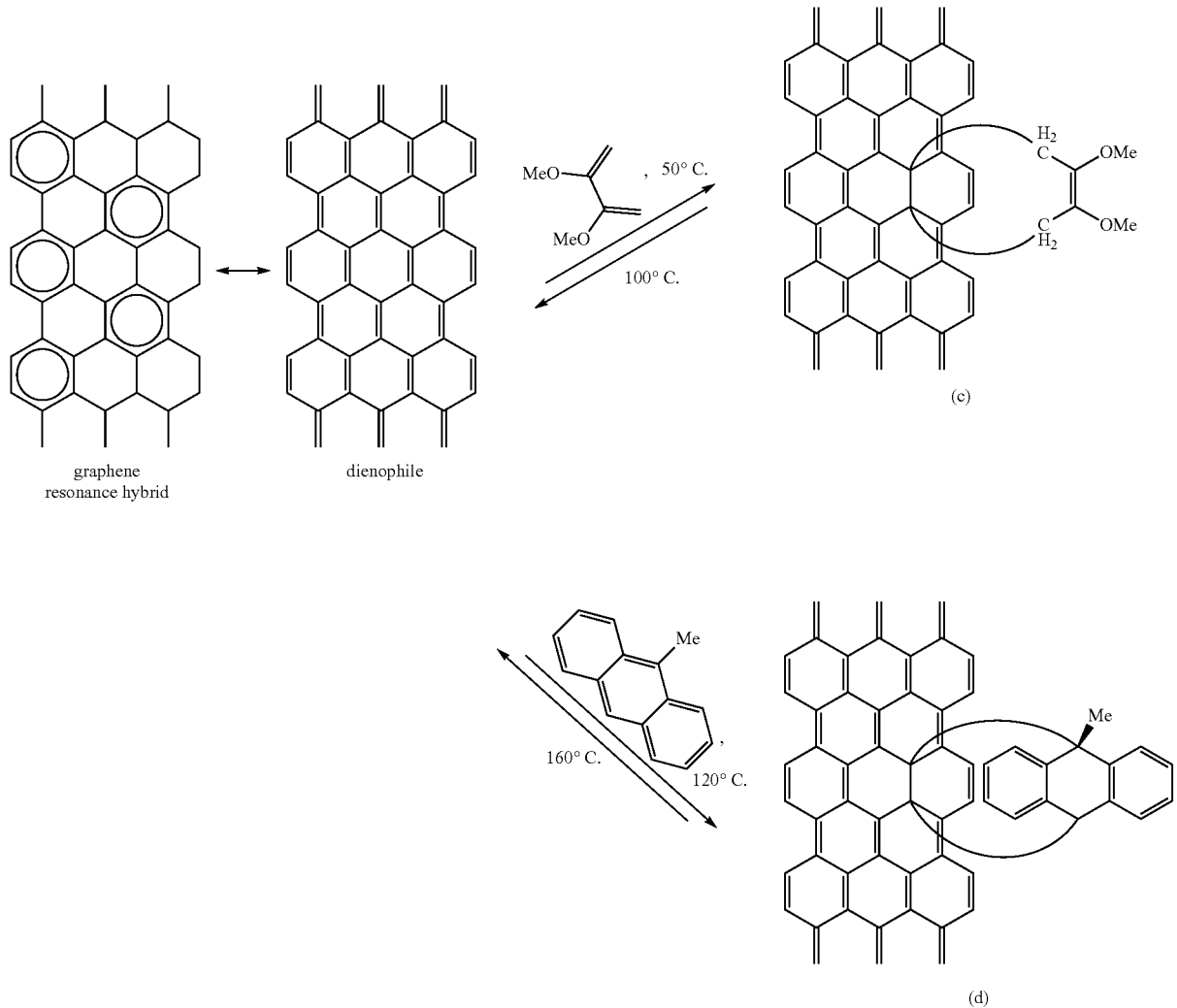

Referring to Reaction Scheme 4, the graphene quantum dots serving as a dienophile may form a compound (c) represented by Formula 7 or a compound (b) represented by Formula 8.

Referring to Reaction Schemes 3 and 4, in the Diels-Alder reaction product of the graphene quantum dots with the diene or dienophile, for convenience of illustration, only one binding site between the graphene quantum dots and the diene and/or between the graphene quantum dots and the dienophile is illustrated. However, a plurality of binding sites may be between the graphene quantum dots and the diene and/or between the graphene quantum dots and the consisting of dimethylacetylene dicarboxylate, acrolein, maleic acid ester, acrylonitrile, fumaric acid ester, maleic anhydride, tetracyanoethylene, benzoquinone, a compound represented by Formula 1, and a group represented by Formula 2.

[Formula 1]

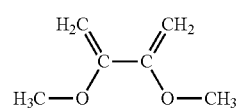

[Formula 2]

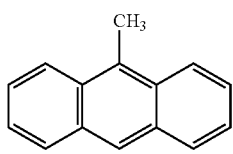

Examples of the maleic acid ester may include dimethyl maleate, diethyl maleate, dibutyl maleate, methyl benzyl maleate, monobutyl maleate, monopentyl maleate, dipentyl maleate, and monopentyl maleate. Examples of the fumaric acid ester may include monopentyl fumarate and dipentyl fumarate.

Examples of the dienophile as a conjugated alkene having an electrophilic functional group may include dimethylacetylene dicarboxylate, acroleine, maleic acid ester, acrylonitrile, fumaric acid ester, maleic anhydride, and tetracycloethylene.

The diene as a compound having at least two double bonds may be, for example, the compound represented by Formula 1 or the compound represented by Formula 2.

The second functional group bound to the graphene quantum dots may be one selected from groups represented in Formula 3.

[Formula 3]

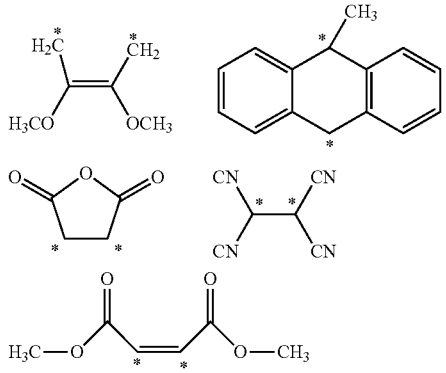

In Formula 3, * denotes a binding site to the graphene quantum dots.

The Diels-Alder reaction product of the graphene quantum dots and the at least one selected from diene and dienophile may be one selected from compounds represented by Formulae 4 to 8.

[Formula 4]

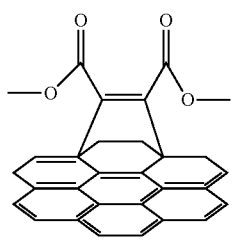

[Formula 5]

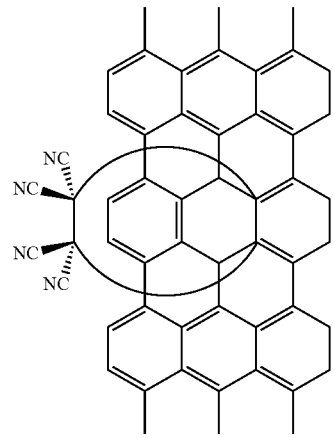

[Formula 6]

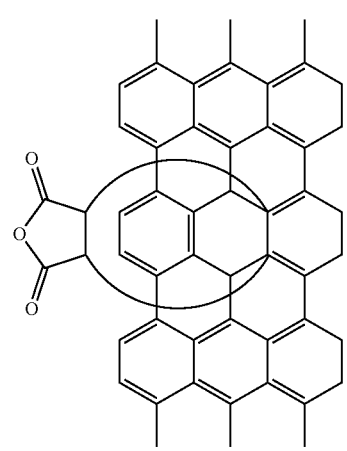

[Formula 7]

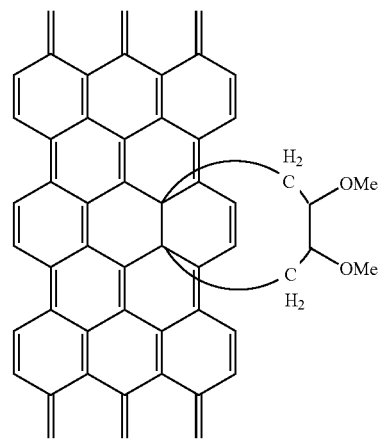

[Formula 8]

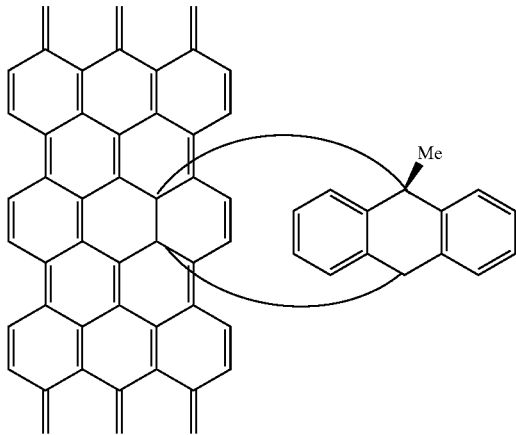

According to another aspect of inventive concepts, a hardmask includes a product resulting from removing the second functional group from the Diels-Alder reaction product of the graphene quantum dots and at least one selected from dienophile and diene. The hardmask may have improved density and thus improved etching resistance relative to a hardmask including common graphene.

The graphene quantum dots (also referred to as "GQDs") may contain an edge carbon (edge C) existing at an edge site and a center carbon (center C) existing at a center site. The edge carbon may have a $sp^3$ binding structure, and the center carbon may have a $sp^2$ binding structure. Since a functional group (e.g., oxygen or nitrogen) may be bound to the edge carbon, the edge carbon may have a higher reactivity to an etching solution relative to the center carbon.

In the GQDs according to one or more embodiments, an amount of the edge carbon may be about 20 atom % or less, for example, in a range of about 1.2 atom % to about 19.1 atom %.

The amounts of the edge carbon and the center carbon in the GQDs may be calculated based on the length of carbon-carbon bonds.

The GQDs may include about 0.01 atom % to about 40 atom % of oxygen, for example, about 10 atom % to about 30 atom % of oxygen. The amount of oxygen may be identified by X-ray photoelectron spectroscopy (XPS). When the amount of oxygen is within these ranges, degassing may not occur during an etching process of the hardmask formed by using the hardmask composition, and the hardmask may have improved etching resistance. When the amount of oxygen in the GQDs is within any of the above-described ranges, the GQDs may have hydrophilic property, and thus an improved adhesive strength to another layer. The GQDs may also have improved dispersibility in a solvent, and preparing the hardmask composition according to embodiments may become easier. In addition, etching resistance to an etching gas may be improved due to a high bond dissociation energy of the functional group including oxygen atom.

The terms "D50", "D90", and "D10" of the graphene quantum dots may refer to particle sizes at volume ratios of 50%, 90%, and 10%, respectively, in a cumulative distribution curve of the graphene quantum dots having different sizes accumulated from smallest to largest. The term "particle size" may refer to an average particle diameter when the graphene quantum dots have a spherical shape, or a length of the major axis when the graphene quantum dots have a non-spherical shape (for example, an elliptical or a rectangular shape).

In the hardmask formed of the hardmask composition according to one or embodiments, light scattering may not occur in a range of visible light, and a transmittance of the hardmask at a wavelength of about 633 nm may be about 99% or higher. In this regard, when a hardmask having improved transmittance is used, identifying a hardmask pattern and an alignment mark for patterning a target etching layer becomes easier, and thus the target etching layer may be patterned to a finer and more compact pattern size.

The GQDs contained in the hardmask may have a k of about 0.5 or lower, for example, about 0.3 or lower, or 0.1 or lower, at a wavelength of about 633 nm. For comparison, k of graphite is in a range of about 1.3 to about 1.5, and k of graphene, which is formed of only $sp^2$ carbon structure, is in a range of about 1.1 to about 1.3.

k is an extinction coefficient which is measured by using a spectroscopic ellipsometer. When k of the GQDs is within the range above and a hardmask formed using the GQDs is used, an alignment mark may be easily detected.

A total thickness of the GQDs may be, for example, in a range of about 0.34 nm to about 100 nm. The GQDs having a thickness within this range may have a stable structure. According to embodiments, the GQDs may contain some oxygen atoms in addition to carbon atoms, rather than having a complete C=C/C—C conjugated structure. A carboxyl group, a hydroxyl group, an epoxy group, or a carbonyl group may be also present at an end of the graphene quantum dots.

The GQDs may have improved solvent dispersibility, and thus may facilitate preparation of a hardmask composition having improved stability. The hardmask including the GQDs may have improved etching resistance against an etching gas.

In the hardmask composition, according to some embodiments, the GQDs may exhibit peaks at about 1340-1350 $cm^{-1}$, about 1580 $cm^{-1}$, and about 2700 $cm^{-1}$ in the Raman spectra. These peaks provide information of a thickness, a crystallinity, and a charge doping status of the GQDs. The peak observed at about 1,580 $cm^{-1}$ is a "G-mode" peak, which is generated in a vibration mode corresponding to stretching of a carbon-carbon bond. Energy of the "G-mode" is determined according to the density of an excess of charges doped in the GQDs. The peak observed at about 2,700 $cm^{-1}$ is a "2D-mode" peak that is useful in evaluating the thickness of the GQDs. The peak observed at about 1,340 $cm^{-1}$ to about 1,350 $cm^{-1}$ is a "D-mode" peak, which appears when a $sp^2$ crystal structure has defects and which is mainly observed when many defects are in a sample or around edges of the sample. An intensity ratio of a D peak to a G peak (a D/G intensity ratio) provides information of a degree of disorder of crystals in the GQDs.

The GQDs may have, as analyzed by Raman spectroscopy, an intensity ratio ($I_D/I_G$) of a D mode peak to a G mode peak of about 2 or less, for example, about 0.001 to about 2.0.

The GQDs may have, as analyzed by Raman spectroscopy, an intensity ratio ($I_{2D}/I_G$) of a 2D mode peak to a G mode peak of about 0.01 or greater, and in some embodiments, about 0.01 to about 1, and in some other embodiments, about 0.05 to about 0.5.

When the intensity ratio ($I_D/I_G$) of a D mode peak to a G mode peak and the intensity ratio ($I_{2D}/I_G$) of a 2D mode peak to a G mode peak are within any of these ranges, the GQDs may have a relatively high crystallinity and relatively few defects, and thus may have an increased binding energy. Accordingly, a hard mask formed using the GQDs may have etching resistance.

According to results of X-ray diffraction analysis with CuKα radiation, the GQDs may have a 2-dimensional (2D) layered structure having a peak corresponding to the (002) crystal plane at about 20° to about 27.°

The GQDs may have an interlayer distance (d-spacing) of about 0.3 nm to about nm, for example, about 0.334 nm to about 0.478 nm, as analyzed by X-ray diffraction analysis. When using the GQDs having a (002) crystal plane peak and a d-spacing within the above-ranges, a hard mask composition having improved etching resistance may be obtained.

In the hard mask composition, according to embodiments, the GQDs may have a higher content of $sp^2$ carbon relative to $sp^3$ carbon and a relatively high content of oxygen, relative to a conventional amorphous carbon layer. A $sp^2$ carbon bond, i.e., a bond of an aromatic structure, may have a higher binding energy than a $sp^3$ carbon bond.

The $sp^3$ structure is a 3-dimensional (3D) binding structure as a regular tetrahedron of carbons likes diamond. The $sp^2$ structure is a 2D binding structure of graphite having an increased ratio of carbon to hydrogen (a C/H ratio), thus ensuring resistance to dry etching.

In the GQDs, according to embodiments, a ratio of an $sp^2$ carbon fraction to an $sp^3$ carbon fraction may be 1 or greater, for example, about 1.0 to about 10, and in some embodiments, 1.88 to 3.42.

An amount of the $sp^2$ carbon atom bonding structure may be about 30 atom % or more, for example, about 39.7 atom % to about 62.5 atom %, as analyzed by stimulated carbon (C1s) XPS. When the mixing ratio of $sp^2$ carbon to $sp^2$ carbon is within these ranges, bond breakage of the GQDs may become difficult due to high carbon-carbon bond energy. Thus, when a hardmask composition including the GQDs is used, etching resistance characteristics may be improved during the etching process. The binding strength between the hardmask and adjacent layers may also be increased.

A hardmask obtained by using conventional amorphous carbon mainly includes a $sp^2$ carbon atom binding structure, and thus has etching resistance but low transparency, causing a hardmask alignment problem and generating a large amount of particles during a deposition process. For these reasons, a hardmask using a diamond-like carbon having a $sp^3$ carbon atom binding structure was developed. However, this hardmask also had a limitation for application to processes due to low etching resistance.

Graphite has a k value of about 1.3 to about 1.5, and graphene having a sp2 structure has a k value of about 1.1 to about 1.3. However, the GQDs according to embodiments may have a k value of about 1.0 or less, for example, about 0.1 to about 0.5 at a desired (and/or alternatively predetermined) wavelength, and thus may good transparency. Thus, when a hardmask including the GQDs according to embodiments is used, an alignment mark may be easily detected during patterning of a target etching layer, so that a finer, more uniform pattern may be formed. The hardmask may also have improved etching resistance.

In the hardmask composition, according to some embodiments, any solvent capable of dispersing GQDs, a diene, or a dienophile may be used. For example, the solvent may be at least one selected from water, an alcoholic solvent, and an organic solvent.

Examples of the alcoholic solvent and organic solvent of the hardmask composition may include methanol, ethanol, and isopropanol. The organic solvent may be, for example, at least one selected from among N-methylpyrrolidone, dichloroethane, dichlorobenzene, dimethylsulfoxide, xylene, aniline, propylene glycol, propylene glycol diacetate, 3-methoxy1,2-propanediol, diethylene glycol, γ-butyrolactone, acetylacetone, cyclohexanone, propylene glycol, monomethyl ether acetate, dichloroethane, O-dichlorobenzene, nitromethane, tetrahydrofuran, nitrobenzene, butyl nitrite, methyl cellosolve, ethyl cellosolve, diethyl ether, diethylene glycol methyl ether, diethylene glycol ethyl ether, dipropylene glycol methyl ether, toluene, hexane, methylethylketone, methyl isopropylketone, hydroxymethylcellulose, and heptane.

The amount of the solvent may be about 100 parts to about 100,000 parts by weight based on 100 parts by weight of a total weight of the GQDs. When the amount of the solvent is within this range, the hardmask composition may have an appropriate viscosity and thus improved film formability.

The hardmask composition according to embodiments may have improved stability.

The hardmask composition may further include: at least one first material selected from an aromatic ring-containing monomer and a polymer containing a repeating unit including an aromatic ring-containing monomer; a second material including at least one selected from a hexagonal boron nitride derivative, a chalcogenide material, a hexagonal boron nitride derivative precursor, and a metal chalcogenide material precursor; or a combination thereof.

The first material may not be combined with the second material, or the first material may be combined with the second material via chemical bonding. The first material and the second material combined via chemical bonding may form a composite structure. The first material and the second material having the aforementioned functional groups may be bound to each other through chemical bonding.

The chemical bonding may be, for example, a covalent bond. The covalent bond may include at least one selected from an ester group (—C(=O)O—), an ether group (—O—), a thioether group (—S—), a carbonyl group ((=C(=O)—), and an amide group (—C(=O)NH—).

The first material and the second material may include at least one selected from the group consisting of a hydroxyl group, a carboxyl group, an amino group, —Si(R$_1$)(R$_2$)(R$_3$) (wherein R$_1$, R$_2$, and R$_3$ are each independently one of hydrogen, a hydroxyl group, a $C_1$-$C_{30}$ alkyl group, a $C_1$-$C_{30}$ alkoxy group, a $C_6$-$C_{30}$ aryl group, a $C_6$-$C_{30}$ aryloxy group, or a halogen atom), a thiol group (—SH), —Cl, —C(=O)Cl, —SCH$_3$, a glycidyloxy group, a halogen atom, an isocyanate group, an aldehyde group, an epoxy group, an imino group, a urethane group, an ester group, an amide group, an imide group, an acryl group, a methacryl group, —(CH$_2$)$_n$COOH (wherein n is an integer from 1 to 10), —CONH$_2$, a $C_1$-$C_{30}$ saturated organic group having a photosensitive functional group, and a $C_1$-$C_{30}$ unsaturated organic group having a photosensitive functional group.

For example, the aromatic ring-containing monomer may be a monomer represented by Formula 8.

[Formula 8]

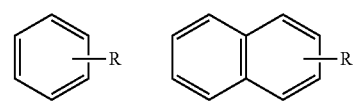

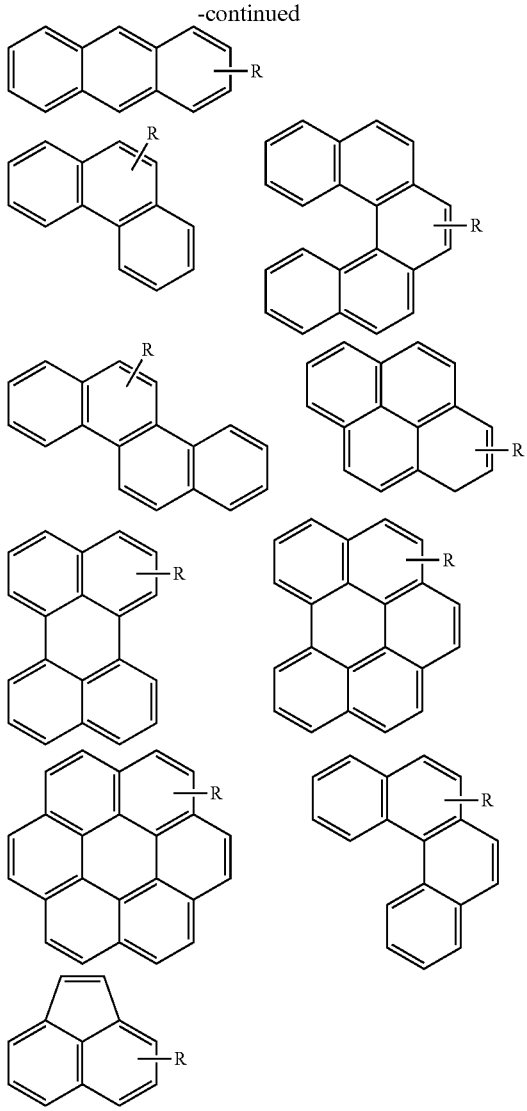

In Formula 8, R may be a mono-substituted or a multi-substituted substituent that is at least one selected from the group consisting of hydrogen, a halogen atom, a hydroxyl group, an isocyanate group, a glycidyloxy group, a carboxyl group, an aldehyde group, an amino group, a siloxane group, an epoxy group, an imino group, a urethane group, an ester group, an epoxy group, an amide group, an imide group, an acryl group, a methacryl group, a substituted or unsubstituted $C_1$-$C_{30}$ saturated organic group, and a substituted or unsubstituted $C_1$-$C_{30}$ unsaturated organic group.

R may be a general photosensitive functional group, in addition to the foregoing groups.

The $C_1$-$C_{30}$ saturated organic group and the $C_1$-$C_{30}$ unsaturated organic group may have a photosensitive functional group. Examples of the photosensitive functional group may include an epoxy group, an amide group, an imide group, a urethane group, and an aldehyde group.

Examples of the $C_1$-$C_{30}$ saturated organic group and the $C_1$-$C_{30}$ unsaturated organic group may include a substituted or unsubstituted $C_1$-$C_{30}$ alkyl group, a substituted or unsubstituted $C_1$-$C_{30}$ alkoxy group, a substituted or unsubstituted $C_2$-$C_{30}$ alkenyl group, a substituted or unsubstituted $C_2$-$C_{30}$ alkynyl group, a substituted or unsubstituted $C_6$-$C_{30}$ aryl group, a substituted or unsubstituted $C_6$-$C_{30}$ aryloxy group, a substituted or unsubstituted $C_2$-$C_{30}$ heteroaryl group, a substituted or unsubstituted $C_2$-$C_{30}$ heteroaryloxy group, a substituted or unsubstituted $C_4$-$C_{30}$ carbocyclic group, a substituted or unsubstituted $C_4$-$C_{30}$ carbocyclic-oxy group, and a substituted or unsubstituted $C_2$-$C_{30}$ heterocyclic group.

In Formula 8, a binding site of R is not limited. Although only one R is included in Formula 8 for convenience of description, R may be substituted at any site where substitution is possible.

For example, the aromatic ring-containing monomer may be a monomer represented by Formula 9.

A-L-A'  [Formula 9]

In Formula 9, A and A' may be identical to or different from each other and may independently be a monovalent organic group derived from one selected from the monomers represented by Formula 8; and L may be a linker which may be a single bond or selected from the group consisting of a substituted or unsubstituted $C_1$-$C_{30}$ alkylene group, a substituted or unsubstituted $C_2$-$C_{30}$ alkenylene group, a substituted or unsubstituted $C_2$-$C_{30}$ alkynylene group, a substituted or unsubstituted $C_7$-$C_{30}$ arylene-alkylene group, a substituted or unsubstituted $C_6$-$C_{30}$ arylene group, a substituted or unsubstituted $C_2$-$C_{30}$ heteroarylene group, a substituted or unsubstituted $C_2$-$C_{30}$ heteroarylene-alkylene group, a substituted or unsubstituted $C_1$-$C_{30}$ alkylene-oxy group, a substituted or unsubstituted $C_7$-$C_{30}$ arylene-alkylene-oxy group, a substituted or unsubstituted $C_6$-$C_{30}$ arylene-oxy group, a substituted or unsubstituted $C_2$-$C_{30}$ heteroarylene-oxy group, a substituted or unsubstituted $C_2$-$C_{30}$ heteroarylene-alkylene-oxy group, —C(=O)—, and —SO$_2$—.

In L, the substituted $C_1$-$C_{30}$ alkylene group, the substituted $C_2$-$C_{30}$ alkenylene group, the substituted $C_2$-$C_{30}$ alkynylene group, the substituted $C_7$-$C_{30}$ arylene-alkylene group, the substituted $C_6$-$C_{30}$ arylene group, the substituted $C_2$-$C_{30}$ heteroarylene group, the substituted $C_2$-$C_{30}$ heteroarylene-alkylene group, the substituted $C_1$-$C_{30}$ alkylene-oxy group, the substituted $C_7$-$C_{30}$ arylene-alkylene-oxy group, the substituted $C_6$-$C_{30}$ arylene-oxy group, the substituted $C_2$-$C_{30}$ heteroarylene-oxy group, the substituted $C_2$-$C_{30}$ heteroarylene-alkylene-oxy group may be substituted with at least one substituent selected from a halogen atom, a hydroxyl group, an isocyanate group, a glycidyloxy group, a carboxyl group, an aldehyde group, an amino group, a siloxane group, an epoxy group, an imino group, a urethane group, an ester group, an epoxy group, an amide group, an imide group, an acryl group, and a methacryl group, or may be substituted with a photosensitive functional group.

The first material may be at least one selected from the group consisting of a compound represented by Formula 10 and a compound represented by Formula 11.

[Formula 10]

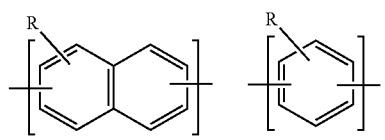

-continued

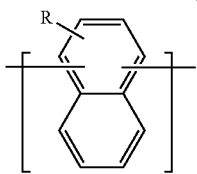

In Formula 10, R may be defined the same as in Formula 8.

[Formula 11]

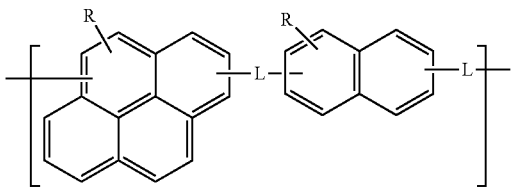

In Formula 11, R may be defined the same as in Formula 8, and L may be defined the same as in Formula 9.

In Formulae 10 and 11, a binding site of R is not limited. Although only one R is included in Formulae 10 and 11 for convenience of description, R may be substituted at any site where substitution is possible.

A weight average molecular weight of the polymer containing a repeating unit including an aromatic ring-containing monomer may be about 300 to about 30,000. When a polymer having a weight average molecular weight within this range is used, a thin film may be more easily formed, and a transparent hardmask may be manufactured.

In one or more embodiments, the first material may be a compound represented by Formula 12:

[Formula 12]

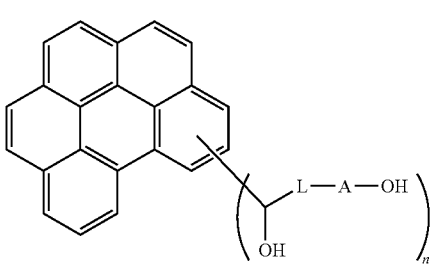

In Formula 12, A may be a substituted or unsubstituted $C_6$-$C_{30}$ arylene group; L may be a single bond or a substituted or unsubstituted C1-C6 alkylene group; and n may be an integer from 1 to 5.

The arylene group may be one selected from groups represented in the following Group 1.

[Group 1]

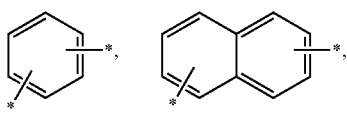

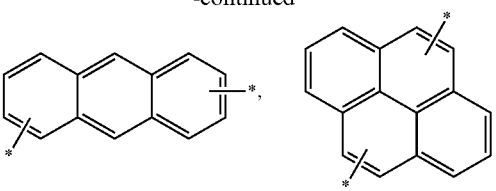

In some embodiments, the compound of Formula 12 may be one selected from compounds represented by Formulae 12a to 12c.

[Formula 12a]

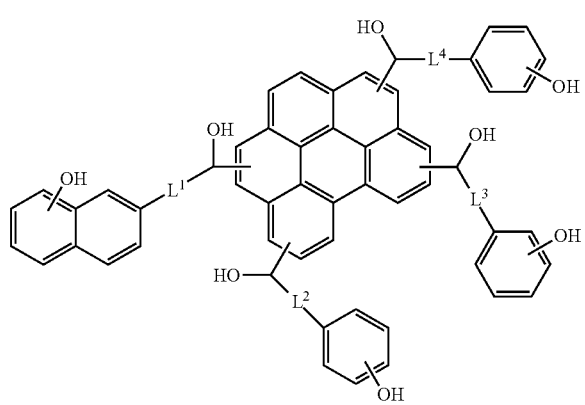

[Formula 12b]

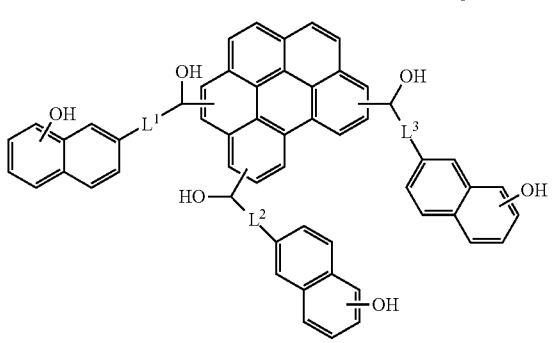

[Formula 12c]

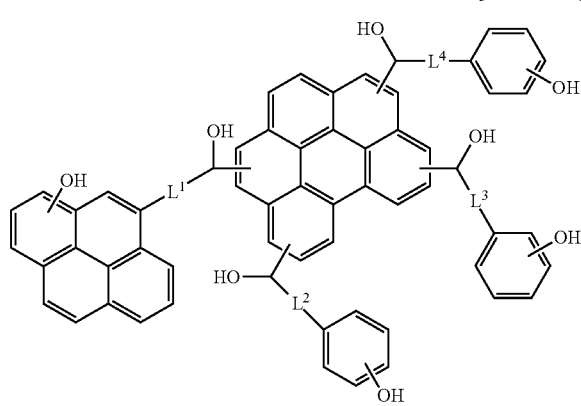

In Formulae 12a, 12b, and 12c, $L^1$ to $L^4$ may each independently be a single bond or a substituted or unsubstituted $C_1$-$C_6$ alkylene group.

The first material may be selected from compounds represented by Formulae 12d to 12f.

[Formula 12d]

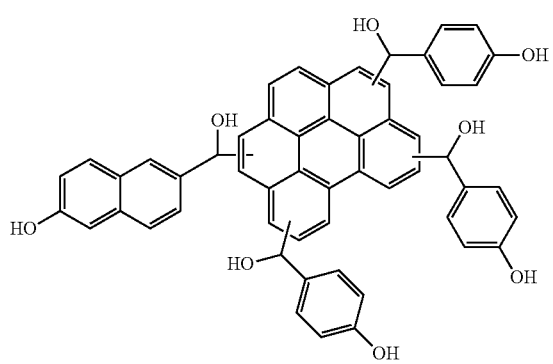

[Formula 12e]

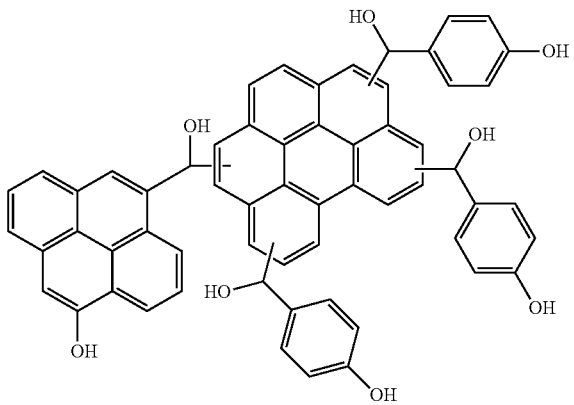

[Formula 12f]

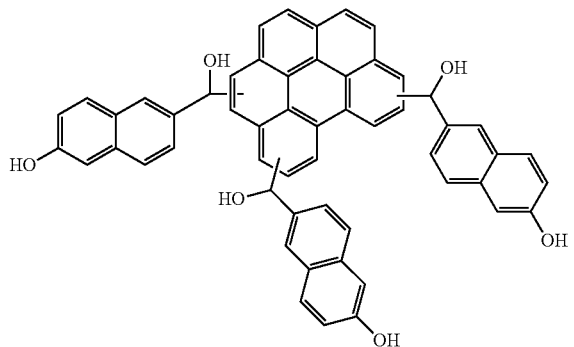

The first material may be a copolymer represented by Formula 13.

[Formula 13]

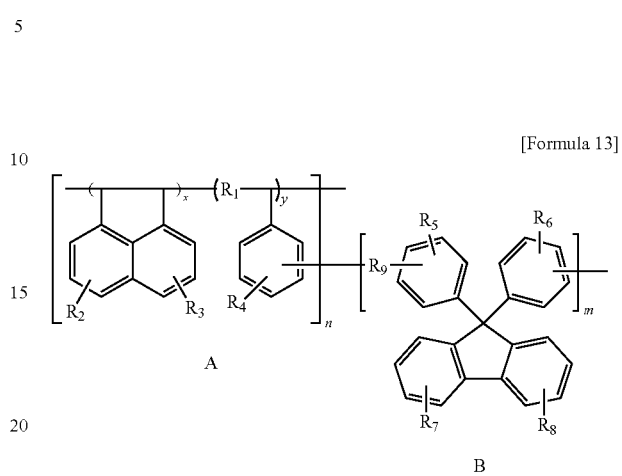

In Formula 13, $R_1$ may be a $C_1$-$C_4$ substituted or unsubstituted alkylene; $R_2$, $R_3$, $R_7$, and $R_8$ may each independently be hydrogen, a hydroxy group, a $C_1$-$C_{10}$ linear or branched cycloalkyl group, an $C_1$-$C_{10}$ alkoxy group, a $C_6$-$C_{30}$ aryl group, or a mixture thereof; $R_4$, $R_5$, and $R_6$ may each independently be hydrogen, a hydroxy group, a $C_1$-$C_4$ alkyl ether group, a phenyldialkylene ether group, or a mixture thereof; and $R_9$ may be a $C_1$-$C_{10}$ alkylene group, a $C_8$-$C_{20}$ phenyldialkylene group, a $C_8$-$C_{20}$ hydroxyphenylalkylene group, or a mixture thereof, wherein x and y may each independently be a mole fraction of two repeating units in part A which is about 0 to about 1, where x+y=1; n may be an integer from 1 to 200; and m may be an integer from 1 to 200.

The second material may be a polymer represented by Formula 13a, or 13b.

[Formula 13a]

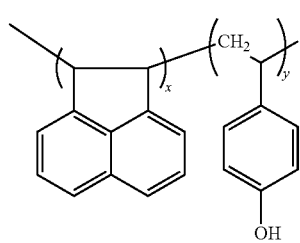

In Formula 13a, x may be 0.2, and y may be 0.8.

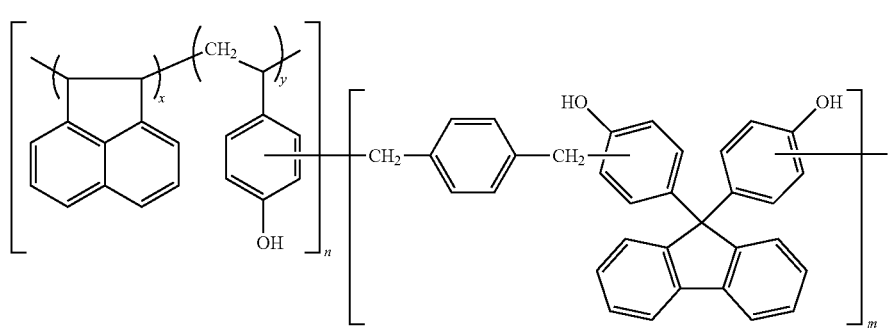
[Formula 13b]

In Formula 13b, x may be 0.2, y may be 0.8, n=90, and m=10.

The first material may be a copolymer represented by Formula 14 or 15.

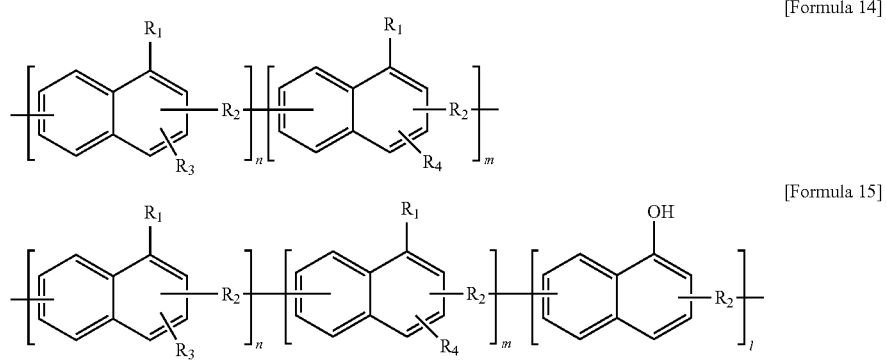
[Formula 14]
[Formula 15]

In Formulae 14 and 15, m and n may each independently be an integer from 1 to 190, $R_1$ may be one selected from hydrogen (—H), a hydroxy group (—OH), a $C_1$-$C_{10}$ alkyl group, a $C_6$-$C_{10}$ aryl group, an allyl group, and a halogen atom, $R_2$ may be one of a group represented by Formula 10A, a phenylene group, a chrysenylene group, a pyrenylene group, a fluoroanthenylene group, an anthronylene group, a benzophenonylene group, a thioxanthonylene group, an anthracenylene group, and their derivatives; $R_3$ may be a conjugated diene group; and $R_4$ may be an unsaturated dienophile.

[Formula 14A]

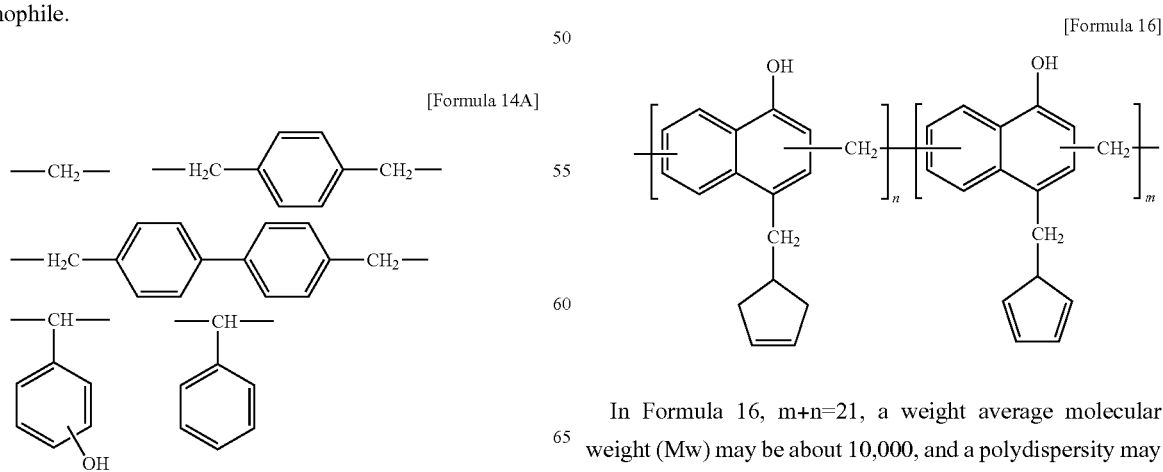

In Formulae 14 and 15, $R_3$ may be, for example, a 1,3-butadienyl group or a 1,6-cyclopentadienylmethyl group, and $R_4$ may be, for example, a vinyl group or a cyclopentenylmethyl group.

The copolymer may be a polymer selected from polymers represented by Formulae 16 to 18.

[Formula 16]

In Formula 16, m+n=21, a weight average molecular weight (Mw) may be about 10,000, and a polydispersity may be 2.1.

[Formula 17]

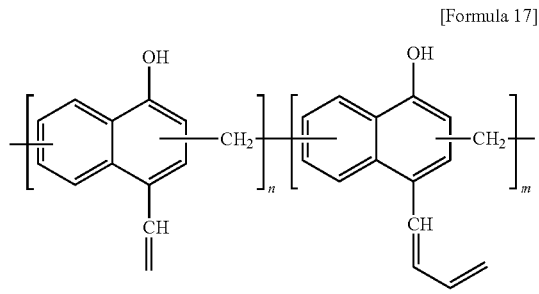

In Formula 17, a weight average molecular weight (Mw) may be about 11,000, a polydispersity (Mw) may be 2.1, and m+n=21.

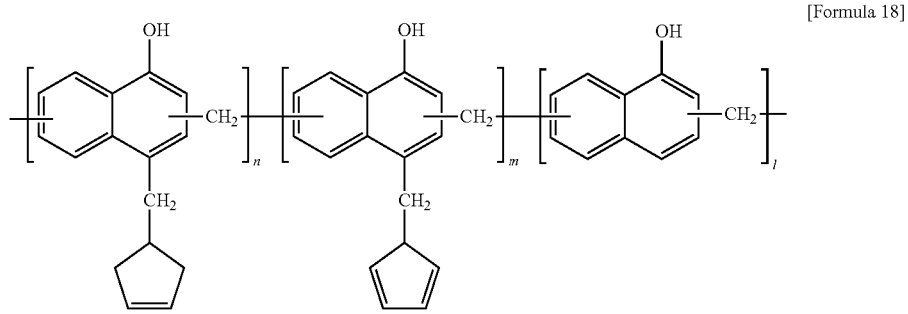

In Formula 18, a weight average molecular weight (Mw) may be about 10,000, a polydispersity may be 1.9, l+m+n=21, and n+m:l=2:1.

[Formula 19]

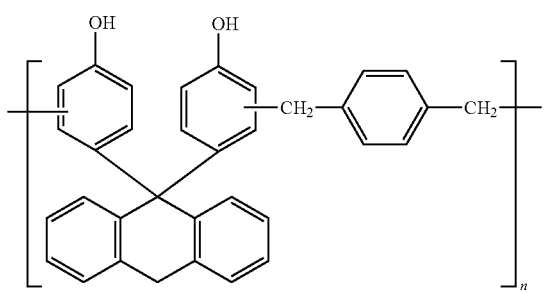

In Formula 19, a weight average molecular weight (Mw) may be about 10,000, a polydispersity may be about 2.0, and n may be about 20.

The GQDs may have a low reactivity to an etching gas, for example, a $C_xF_y$ gas, used for etching a material layer such as a $SiO_2$ or SiN layer, and thus improve etching resistance. When using a $SF_6$ or $XeF_6$ gas as an etching gas having a low reactivity to $SiO_2$ and $SiN_x$, ashing may be facilitated due to improved etching characteristics. In addition, due to transparency of the GQDs, the overall process may be facilitated without need to use an additional alignment mark.

In the hardmask composition, according to some embodiments, the hexagonal boron nitride derivative is a hexagonal boron nitride (h-BN) or a hexagonal boron carbonitride (h-$B_xC_yN_z$) (wherein the sum of x, y, and z may be 3). In the hexagonal boron nitride derivative, boron and nitrogen atoms may be included in a regular fashion in a hexagonal ring, or some of the boron and nitrogen atoms may be substituted with carbon atoms while the hexagonal ring is maintained.

In the hardmask composition, according to some embodiments, the metal chalcogenide material may be a compound including at least one Group 16 (chalcogen) element and at least one electropositive element. For example, the metal chalcogenide material may include at least one metal element selected from molybdenum (Mo), tungsten (W), niobium (Nb), vanadium (V), tantalum (Ta), titanium (Ti), zirconium (Zr), hafnium (Hf), technetium (Tc), rhenium (Re), copper (Cu), gallium (Ga), indium (In), tin (Sn), germanium (Ge) and lead (Pb), and one chalcogen element selected from sulfur (S), selenium (Se), and tellurium (Te).

The metal chalcogenide material may be selected from molybdenum sulfide ($MoS_2$), molybdenum selenide ($MoSe_2$), molybdenum telluride ($MoTe_2$), tungsten sulfide ($WS_2$), tungsten selenide ($WSe_2$), and tungsten telluride ($WTe_2$). In some embodiments, the chalcogenide material may be molybdenum sulfide ($MoS_2$).

The hexagonal boron nitride derivative may have a flat hexagonal crystal structure, the vertices of which are occupied alternatively by boron and nitrogen atoms. A layered structure of the hexagonal boron nitride derivative is a structure in which adjacent boron and nitrogen atoms overlap each other due to their polarities, which is also called "a AB stacking" structure. The hexagonal boron nitride derivative may have a layered structure of nanoscale thin sheets stacked one upon another, or may include a single layer or multiple layers of hexagonal boron nitride derivative sheets separated or delaminated from the layered structure.

The hexagonal boron nitride derivative according to one or more embodiments may have a peak at about 1360 cm$^{-1}$ in the Raman spectra. This location of the peak may give information about the number of layers in the hexagonal boron nitride derivative. Through atomic force microscope (AFM) analysis, Raman spectroscopy analysis, transmission electron microscope (TEM) analysis, or the like, it may be found that the hexagonal boron nitride has a single-layered or multilayered nanosheet structure.

According to a result of X-ray diffraction analysis with CuKα radiation, the hexagonal boron nitride may include a 2-dimensional (2D) layered structure having a (002) crystal plane peak. The (002) crystal plane peak may be observed in a range of about 20° to about 27°.

An interlayer distance (d-spacing) of the hexagonal boron nitride obtained by X-ray diffraction analysis may be in a range of about 0.3 nm to about 0.7 nm, for example, about 0.334 nm to about 0.478 nm. An average particle diameter of crystals of the hexagonal boron nitride obtained by X-ray diffraction analysis may be about 1 nm or greater, for example, in a range of about 23.7 Angstroms (Å) to about 43.9 Å. When the interlayer distance (d-spacing) is within this range, the hardmask composition may have improved etching resistance.

The hexagonal boron nitride may include a single layer of 2D boron nitride or a stack of multiple layers of 2D boron nitride.

Hereinafter, a method of forming a hardmask by using the hardmask composition according to any of the embodiments will be described in detail.

In some embodiments, the hardmask composition may include one selected from GQDs, at least one selected from diene and dienophile, and a solvent. In some other embodiments, the hardmask composition may include a Diels-Alder reaction product of GQDs and diene, a Diels-Alder reaction product of GQDs and dienophile, and a solvent.

In some other embodiments, the hardmask composition may include a product of thermally treating a Diels-Alder reaction product of GQDs and at least one selected from diene and dienophile, and a solvent.

A hardmask according to some embodiments may be formed by coating the hardmask composition on a target etching layer and drying the same.

The GQDs as a starting material may be, for example, OH-functionalized GQDs, COOH-functionalized graphene nanoquantum dots (COOH-functionalized GQDs), or a graphene quantum dot (GQD) precursor.

Optionally, during or after the process of coating the hardmask composition on a target etching layer, heat treatment may be performed. The heat treatment may also be omitted. Conditions for the heat treatment may be varied depending on a material of the target etching layer. For example, the heat treatment may be performed at a temperature ranging from room temperature (about 20° C. to 25° C.) to about 1500° C.

The heat treatment may be performed in an inert gas atmosphere or in vacuum.

The heat treatment may be performed using induction heating, radiant heat, lasers, infrared rays, microwaves, plasma, ultraviolet rays, or surface plasmon heating as a heat source.

The inert gas atmosphere may be created by using a mixture a nitrogen gas and/or an argon gas.

After the thermal treatment of removing the solvent, a process of c-axial alignment of graphene may be performed.

After the heat treatment, the solvent may be removed. The resulting product of removing the solvent through or without the thermal treatment may be subjected to a baking process at a temperature of about 400° C. or lower, for example, about 100° C. to about 400° C. After the thermal treatment, further heat treatment may be performed at a temperature of about 800° C. or lower, for example, in a range of about 400° C. to about 800° C.

A thermal reduction process may occur during the heat treatment. Through the thermal reduction process, an oxygen content of the GQDs may be reduced.

In some embodiments, the baking process may be omitted, and only the thermal treatment may be performed.

When the temperatures of the heat treatment and the baking process are within the above ranges, a hardmask having improved etching resistance may be formed.

In the thermal treatment and the baking process, a temperature increasing rate may be about 1° C./min to about 10° C./min. When the temperature increasing rate is within this range, process efficiency may be improved without concern about damage of a deposited layer from sudden temperature changes.

In some embodiments, the hardmask may have a thickness of about 10 nm to about 10,000 nm.

Hereinafter, methods of preparing graphene quantum dots, according to embodiments, will be described in detail.

According to a first preparation method, a graphite intercalation compound (GIC) may be obtained by intercalating an interlayer intercalation material into graphite, and then graphene quantum dots may be obtained from the GIC.

The interlayer intercalation material may be, for example, potassium sodium tartrate. When potassium sodium tartrate is used as the interlayer intercalation material, the material may be intercalated into graphite without an additional surfactant or a solvent during a solvo-thermal reaction to obtain the GIC, and then desired GQDs may be obtained via a process of sorting particle sizes of the resultant. Potassium sodium tartrate may serve as an interlayer intercalation material and a solvent at the same time.

The solvo-thermal reaction may be performed in, for example, an autoclave. The solvo-thermal reaction may be performed at a temperature, for example, in a range of about 25° C. to about 400° C., or, for example, at about 250° C.

Examples of graphite as a starting material may include natural graphite, kish graphite, synthetic graphite, expandable graphite or expanded graphite, or a mixture thereof.

A second preparation method is a method of preparing GQDs having a functional ground bound thereto, wherein the functional group may be, for example, a hydroxy group. Hydroxy group (OH)-functionalized GQDs may have good solubility in a solvent and thus have a wide range of application fields.

According to some embodiments, hydroxyl group-functionalized GQDs may be prepared as follows.

Graphene quantum dots having a single crystal may be obtained by performing a hydrothermal fusion reaction on a polycyclic aromatic hydrocarbon under an alkaline aqueous solution.

The hydrothermal reaction under an alkali aqueous solution condition may be performed at a temperature in a range of about 90° C. to about 200° C. In the hydrothermal reaction, when alkaline species such as $OH^-$ are present, removal of hydrogen, condensation or graphitization, and edge functionalization may occur.

Examples of the polycyclic aromatic hydrocarbon may include a pyrene and a 1-nitropyrene.

Before the hydrothermal reaction, a nitration reaction may be performed on the polycyclic aromatic hydrocarbon. The nitration reaction may be performed using a hot nitrate (hot $HNO_3$).

During the hydrothermal reaction, an amine material such as $NH_3$ or $NH_2NH_2$ may be added. When such an amine material is added, water-soluble $OH^-$ and an amine-functionalized GQDs may be obtained.

According to a third preparation method, GQDs may be obtained by acid-treating graphite. For example, an acid and an oxidizing agent may be added to graphite, heated and allowed to react, and cooled down to room temperature (25° C.) to obtain a graphene quantum dot precursor-containing mixture. An oxidizing agent may be added to the precursor-containing mixture for an oxidation process, and the resultant from the oxidation process may be subjected to a work-up process to prepare target GQDs.

Examples of the acid may include sulfuric acid, nitric acid, acetic acid, phosphoric acid, hydrofluoric acid, perchloric acid, trifluoroacetic acid, hydrochloric acid, m-chlorobenzoic acid, and a mixture thereof. Examples of the oxidizing agent may include potassium permanganate, potassium perchlorate, ammonium persulfate, and a mixture thereof. An amount of the oxidizing agent may be in a range of about 0.00001 parts to about 30 parts by weight based on 100 parts by weight of graphite.

The heating followed by adding an acid and an oxidizing agent to graphite may be performed, for example, by using microwaves. The microwaves may have a power output of about 50 W to about 1500 W and a vibration frequency of about 2.45 GHz to about 60 GHz. The period of time for which the microwaves are applied may vary depending on a vibration frequency of the microwaves. For example, the microwaves may be applied for about 10 minutes to about 30 minutes.

The work-up process includes controlling the temperature of the resultant from the oxidizing process to room temperature, adding deionized water to dilute the resultant, and adding a base thereto for neutralization of the resultant.

Thereafter, work-a process of shorting particle sizes from the resultant to obtain target GQDs may be performed.

Hereinafter, a method of forming a pattern by using a hardmask composition according to some embodiments will be described with reference to FIGS. 2A to 2E.

Figure 2A:
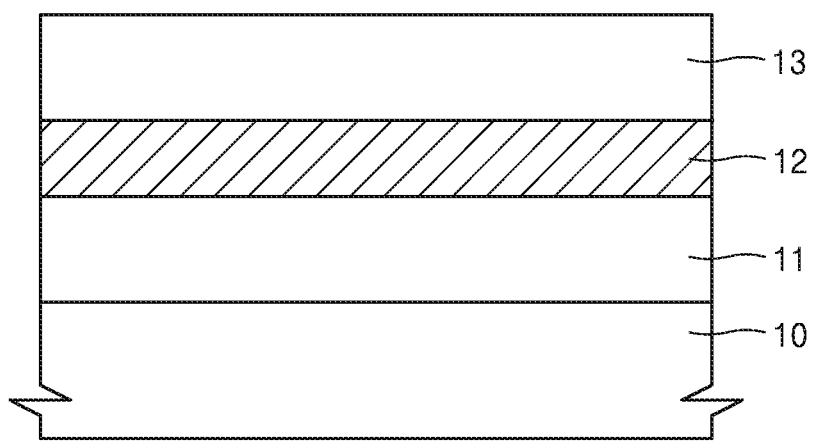
FIGS. 2A to 2E are cross-sectional views for explaining a method of forming a pattern, according to some embodiments, using a hardmask composition according to some embodiments.

Referring to FIG. 2A, a target etching layer 11 that is to be etched may be formed on a substrate 10. A hardmask composition according to any of the above-described embodiments may be provided on the target etching layer 11 in order to form a hardmask layer 12.

The process of providing the hardmask composition may be performed by one method selected from spin coating, air spraying, electrospraying, dip coating, spray coating, doctor-blade coating, and bar coating In some embodiments, the providing of the hardmask composition may be performed by using a spin-on coating method. The hardmask composition may be coated on the substrate 10 to a thickness of, for example, in a range of about 10 nm to about 10,000 nm, or about 10 nm to about 1,000 nm. However, embodiments are not limited thereto.

The substrate 10 is not particularly limited. For example, the substrate 10 may be at least one selected from a Si substrate; a glass substrate; a GaN substrate; a silica substrate; a substrate including at least one selected from nickel (Ni), cobalt (Co), iron (Fe), platinum (Pt), palladium (Pd), gold (Au), aluminum (Al), chromium (Cr), copper (Cu), manganese (Mn), molybdenum (Mo), rhodium (Rh), iridium (Ir), tantalum (Ta), titanium (Ti), tungsten (W), uranium (U), vanadium (V), and zirconium (Zr); and a polymer substrate.

A photoresist layer 13 may be formed on the hardmask layer 12.

Figure 2B:
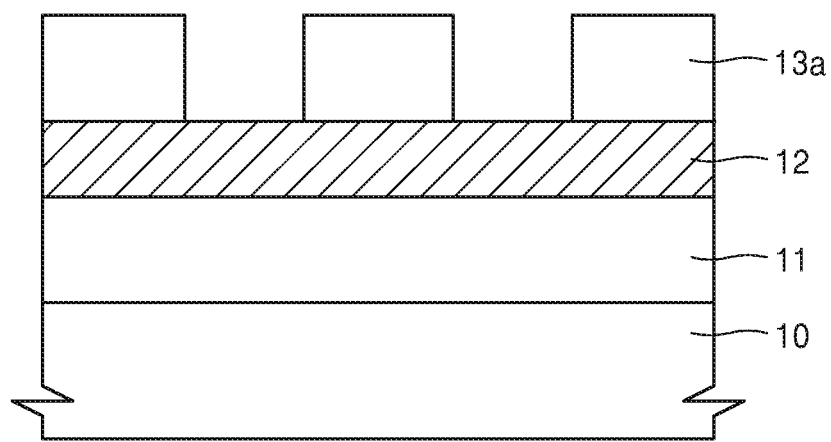

Referring to FIG. 2B, a photoresist pattern 13a may be formed by exposing and developing the photoresist layer 13 by using a common method in the art.

The process of exposing the photoresist layer 13 may be performed by using, for example, argon fluoride (ArF), krypton fluoride (KrF), or extreme ultraviolet (EUV) laser. After the exposure process, a heat treatment may be performed at a temperature in a range of about 200° C. to about 500° C.

In the developing process, a developing solution such as an aqueous solution of tetramethylammonium hydroxide (TMAH) may be used.

Figure 2C:
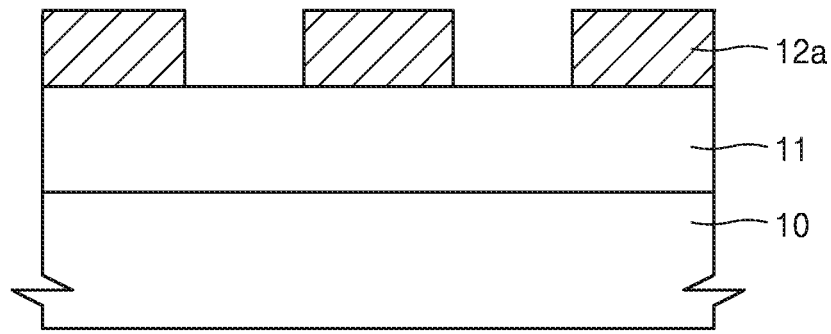

Next, the hardmask layer 12 may be etched by using the photoresist pattern 13a as an etch mask, to thereby form a hardmask pattern 12a on the target etching layer 11 (see FIG. 2C).

A thickness of the hardmask pattern 12a may be in a range of about 10 nm to about 10,000 nm. When the thickness of the hardmask pattern 12a is within this range, the hardmask pattern 12a may have improved film uniformity and improved etching resistance.

For example, the etching process may be performed by using a dry etching method using an etching gas. Examples of the etching gas may include at least one selected from $CF_4$, $CHF_3$, $Cl_2$, and $BCl_3$.

In some embodiments, when a mixture gas of $C_4F_8$ and $CHF_3$ is used as the etching gas, a mixing ratio of $C_4F_8$ and $CHF_3$ may be in a range of about 1:10 to about 10:1 by volume.

The target etching layer 11 may be patterned into a plurality of patterns. The plurality of patterns may include various types of patterns, for example, a metal pattern, a semiconductor pattern, and an insulating pattern. For example, the plurality of patterns may be used as various patterns in a semiconductor integrated circuit device.

The target etching layer 11 may be formed of a material of a target final pattern. For example, the target etching layer 11 may be a metal layer including aluminum or copper, a semiconductor layer including silicon, or an insulating layer including silicon oxide or silicon nitride. The target etching layer 11 may be formed by using various methods such as sputtering, electronic beam deposition, chemical vapor deposition, or physical vapor deposition. For example, the target etching layer 11 may be formed by using a chemical vapor deposition method.

Figure 2D:
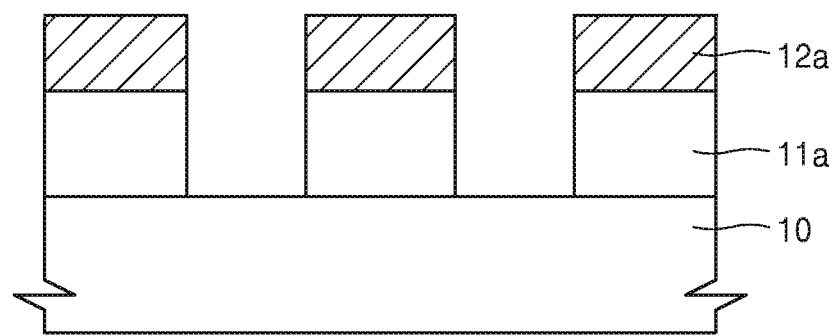
Figure 2E:
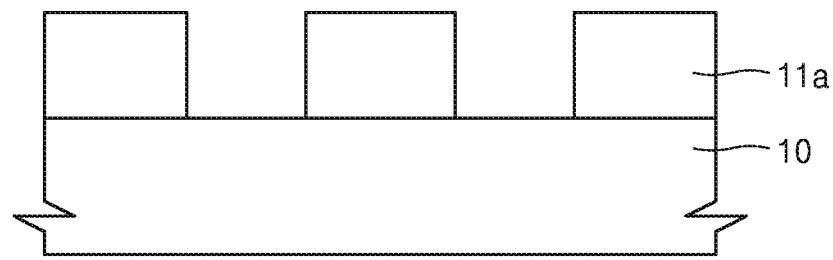

Referring to FIGS. 2D and 2E, the target etching layer 11 may be etched by using the hardmask pattern 12a as an etch mask to form a target etching layer pattern 11a having a desired fine pattern.

When the hardmask composition according to one or more embodiments is used, a solution process may be applicable without need for additional coating equipment, ashing-off under oxygen atmosphere may be facilitated, and the resulting pattern may have improved physical characteristics.

In some embodiments, the hardmask may include a product resulting from thermally treating a Diels-Alder reaction product of the GQDs and at least one selected from a diene and a dienophile.

The hardmask according to one or more embodiments may be used as an etch mask or as a stopper in the manufacture of a semiconductor device by being disposed between other layers.

Hereinafter, a method of forming a pattern by using a hardmask composition according to one or more embodiments will be described with reference to FIGS. 3A to 3D.

Figure 3A:
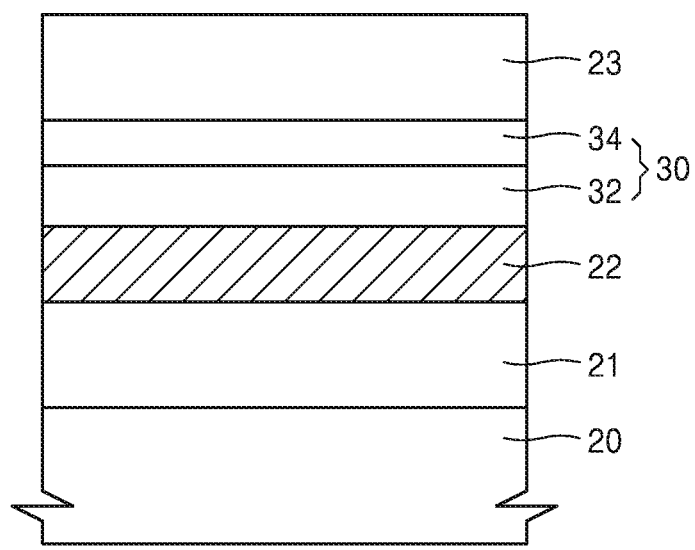
FIGS. 3A to 3D are cross-sectional views for explaining a method of forming a pattern, according to another embodiment, using a hardmask composition according to some embodiments.

Referring to FIG. 3A, a target etching layer 21 may be formed on a substrate 20. The substrate 20 may be a silicon substrate.

The target etching layer 21 may be formed as, for example, a silicon oxide layer, a silicon nitride layer, a silicon nitroxide layer, a silicon carbide (SiC) layer, or a derivative layer thereof. Then, a hardmask composition according to any one of the above-describe embodiments may be provided on the target etching layer 21 to form a hardmask layer 22.

Figure 3B:
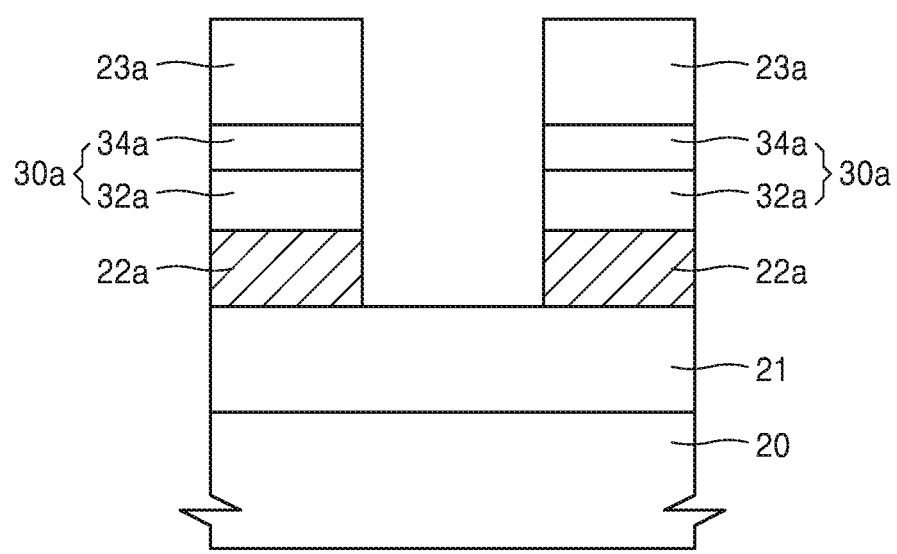
Figure 3C:
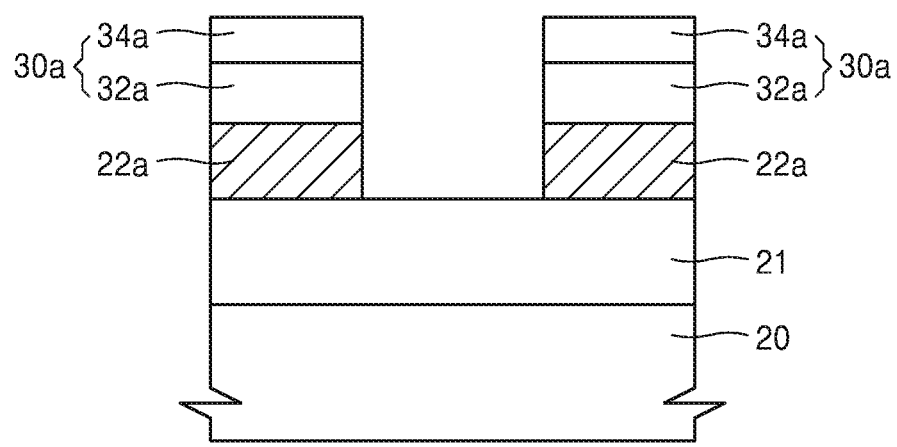

An anti-reflection layer 30 may be formed on the hardmask layer 22. The anti-reflection layer 30 may be an inorganic anti-reflection layer, an organic anti-reflection layer, or a combination thereof. FIGS. 3A to 3C illustrate embodiments in which the anti-reflection layer 30 includes an inorganic anti-reflection layer 32 and an organic anti-reflection layer 34.

The inorganic anti-reflection layer 32 may be, for example, a SiON layer. The organic anti-reflection layer 34 may be a polymer layer commonly used in the art having an appropriate refractive index and a high absorption coefficient with respect to a wavelength of light to which a photoresist is exposed. A thickness of the anti-reflection layer 30 may be, for example, in a range of about 100 nm to about 500 nm.

Next, a photoresist layer 23 may be formed on the anti-reflection layer 30.

The photoresist layer 23 may be exposed to light and then developed using a common method, to thereby form a photoresist pattern 23a. Then, the anti-reflection layer 30 and the hardmask layer 22 may be sequentially etched by using the photoresist pattern 23a as an etch mask to form a hardmask pattern 22a on the target etching layer 21. The hardmask pattern 22a may include an inorganic anti-reflection pattern 32a and an organic anti-reflection pattern 34a.

Although in FIG. 3B the photoresist pattern 23a and an anti-reflection pattern 30a are remaining on the hardmask pattern 22a after the formation of the hardmask pattern 22a, the photoresist pattern 23a and the anti-reflection pattern 30a may be partially or completely removed during the etching process for forming the hardmask pattern 22a.

FIG. 3C illustrates the state after removing only the photoresist pattern 23a.

Figure 3D:
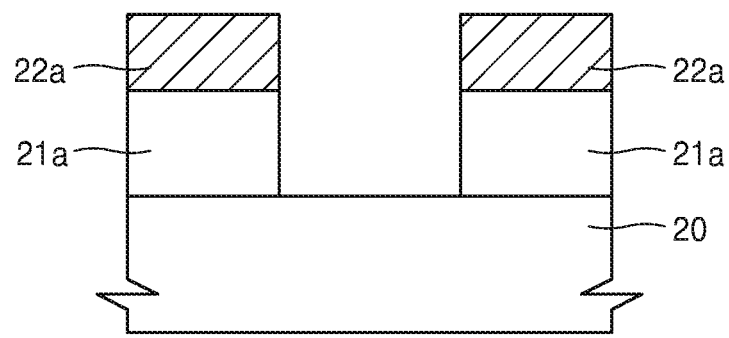

The target etching layer 21 may be etched by using the hardmask pattern 22a as an etch mask to form a desired layer pattern, which is a target etching layer pattern 21a (see FIG. 3D).

As described above, the hardmask pattern 22a may be removed after the target etching layer pattern 21 is formed. According to one or more embodiments, the hardmask pattern 22a may be easily removed by using a common method in the art, and almost no residue remains after the hardmask pattern 22a is removed.

The removing of the hardmask pattern 22a may be performed by, but not limited to, $O_2$ ashing and wet stripping. For example, the wet stripping may be performed using alcohol, acetone, or a mixture of nitric acid and sulfuric acid.

The GQDs in the hardmask formed according to the above processes may have a higher content of $sp^2$ carbon structures than $sp^3$ carbon structures, and thus the hardmask may have sufficient resistance to dry etching. The hardmask may also have improved transparency, and thus an alignment mark for patterning may be easily detected.

According to some embodiments, a hardmask formed using a hardmask composition according to any of the embodiments may be used in manufacturing and designing an integrated circuit device according in a semiconductor device manufacturing process. For example, the pattern may be used in forming a patterned material layer structure such as metal wirings, holes for contact or bias, insulation sections (for example, a damascene trench (DT) or shallow trench isolation (STI)), or a trench for a capacitor structure.

One or more embodiments of the present disclosure will now be described in detail with reference to the following examples. However, these examples are only for illustrative purposes and are not intended to limit the scope of the one or more embodiments of the present disclosure.

Preparation Example 1

Preparation of Graphene Quantum Dots 20 mg of graphite (available from Aldrich Co., Ltd.) and 100 mg of potassium sodium tartrate were added to an autoclave vessel and then reacted at a temperature of 250° C. for about 60 minutes.

Once the reaction was complete, the resultant was centrifuged using a centrifugal filter (8,000 nominal molecular weight limit (NMWL) and 10,000 NMWL, Amicon Ultra-15) to sort out a particle size, which was then subjected to dialysis to remove residues. Then the resultant was dried to thereby obtain graphene quantum dots (GQDs) in a sheet form having a major-axis length of about 7 nm.

Preparation Example 2

Preparation of Graphene Quantum Dots 20 mg of graphite (available from Alfa Aesar Co., Ltd.) was dissolved in 100 mL of concentrated sulfuric acid, and the mixture was sonicated for about 1 hour. 1 g of $KMnO_4$ was added to the resulting mixture, and a temperature of the reaction mixture was adjusted to be about 25° C. or lower.

Microwaves (having a power of about 600 W) were applied to the resultant at an atmospheric pressure under reflux for about 10 minutes. The reaction mixture was cooled down to adjust a temperature of the reaction mixture to about 25° C., and then 700 mL of deionized water was added to the reaction mixture to dilute the reaction mixture. Next, a sodium hydroxide was added to the reaction mixture in an ice bath to adjust a pH of the reaction mixture to about 7.

The reaction mixture was filtered through a porous membrane having a pore diameter of about 200 nm to separate and remove graphene quantum dot having a large size. The resulting filtrate was subjected to dialysis to remove residues, and the resultant was dried to obtain graphene quantum dots in a sheet form having a major-axis length of about 7 nm.

Preparation Example 3

Preparation of OH-Functionalized Graphene Quantum Dot (OH-Bound Graphene Quantum Dot)

160 mL of nitric acid was added to 2 g of pyrene, and the mixture was refluxed at a temperature of about 80° C. for about 12 hours to obtain a reaction mixture containing 1,3,6-trinitropyrene. The reaction mixture was cooled down to room temperature, and 1 L of deionized water was added to dilute the reaction mixture. Subsequently, the reaction mixture was filtered through a microporous membrane having a pore size of about 0.22 μm.

1.0 g of 1,3,6-trinitropyrene obtained through the filtration was dispersed in 0.6 L of a 0.2M NaOH aqueous solution, and ultrasonic waves (500 W, 40 kHz) were then applied thereto for about 2 hours to obtain a suspension. The obtained suspension was put into an autoclave vessel and then reacted at a temperature of about 200° C. for about 10 hours. The resultant was cooled down to room temperature, and filtered through a microporous membrane having a pore size of about 0.22 μm to remove an insoluble carbon product. The resulting product obtained through the filtration was then subjected to dialysis for 2 hours to obtain OH-functionalized graphene quantum dots in a sheet form having a major-axis length of about 7 nm.

The graphene quantum dots prepared in Preparation Examples 1 and 3 had a structure including an oxygen-containing functional group at an end thereof. The graphene quantum dots prepared in Preparation Example 2 had a structure including an oxygen-containing functional group both at an edge and plane of graphene quantum dot thereof due to the use of microwaves during the preparation process.

Preparation Example 4

Preparation of COOH-Functionalized Graphene Quantum Dots

Chloroacetic acid was added to the OH-functionalized graphene quantum dots prepared in Preparation Example 3, followed by heat treatment at a temperature of 80° C. for 60 minutes, and then a coupling reaction to thereby obtain COOH-functionalized graphene quantum dots having a major-axis length of about 7 nm.

Example 1

Preparation of Hardmask Composition

The OH-functionalized GQDs (having a size of about 7 nm) obtained according to Preparation Example 3 was mixed with dimethylacetylene dicarboxylate (DA) to prepare a hardmask composition. A mixed weight ratio of the OH-functionalized GQDs of Preparation Example 3 to dimethylacetylene dicarboxylate in the hardmask composition was about 1:5 by weight.

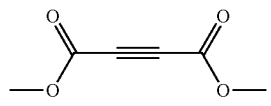

DA

Example 2

Preparation of Hardmask Composition

A hardmask composition was prepared in the same manner as in Example 1, except that maleic anhydride represented by Formula 20 was used instead of dimethylacetylene dicarboxylate.

[Formula 20]

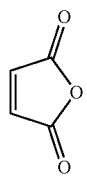

Example 3

Preparation of Hardmask Composition

A hardmask composition was prepared in the same manner as in Example 1, except that tetracyanoethylene represented by Formula 21 was used instead of dimethylacetylene dicarboxylate.

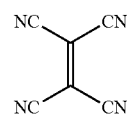

[Formula 21]

Example 4

Preparation of Hardmask Composition

A hardmask composition was prepared in the same manner as in Example 1, except that a mixed weight ratio of the OH-functionalized GQDs of Preparation Example 3 to dimethylacetylene dicarboxylate in the hardmask composition was about 1:1 by weight.

Manufacturing Example 1

Manufacture of Silicon Substrate Having Silicon Oxide Layer Pattern

The hardmask composition according to Example 1 was spin-coated on a silicon substrate having a silicon oxide layer (see Reaction Scheme 5) and then backed at about 400° C. for about 2 minutes, to thereby form a hardmask having a thickness of about 465 nm and including a product of the thermal treatment of a Diels-Alder reaction product of the OH-functionalized GQDs and dimethylacetylene dicarboxylate (DA).

[Reaction Scheme 5]

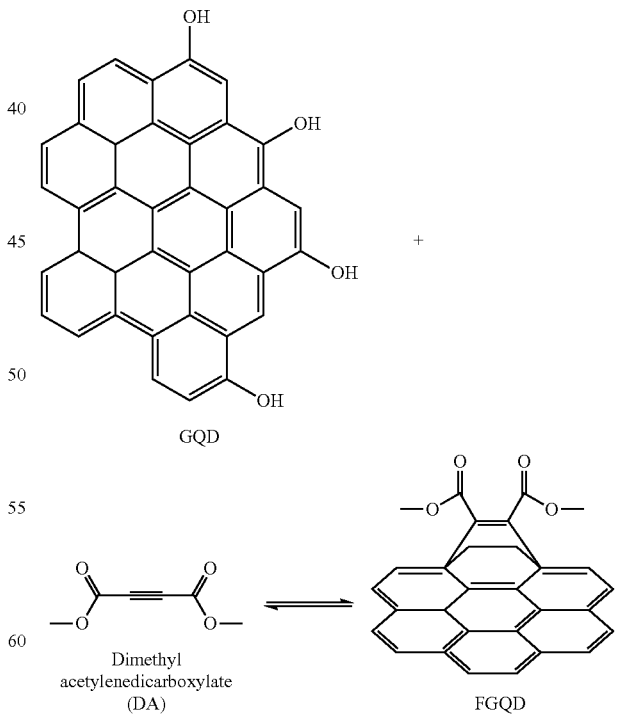

In Reaction Scheme 5, for convenience of illustration, hydroxyl groups (—OH) bound to the GQDs were omitted in the FGQD.

An ArF photoresist (PR) was coated on the hardmask to a thickness of about 1700 Å and then pre-baked at a temperature of about 110° C. for about 60 seconds. The resultant was exposed to light by using a light exposing instrument (available from ASML, XT: 1400, and NA 0.93), post-baked at a temperature of about 110° C. for about 60 seconds, and then developed by using a 2.38 wt % aqueous solution of tetramethyl ammonium hydroxide (TMAH) to form a photoresist pattern.

Dry etching was performed using the photoresist pattern as a mask and a $CF_4/CHF_3$ mixture gas. The etching conditions included 20 mT of a chamber pressure, 1800 W of a RF power, a ratio of $C_4F_8$ to $CHF_3$ in 4:10 by volume, and an etching time of about 120 seconds.

$O_2$ ashing and wet stripping were performed on a hardmask and an organic material remaining after the dry etching to thereby obtain a desired silicon substrate having a silicon oxide layer pattern as a final pattern.

Manufacturing Examples 2-4

Manufacture of Silicon Substrate Having Silicon Oxide Layer Pattern

Silicon substrates having a silicon oxide layer pattern were manufactured in the same manner as in Example 1, except that the hardmask compositions prepared according to Examples 2 to 4 were used, respectively, instead of the hardmask composition of Example 1.

Comparative Example 1

A monomer represented by Formula 6a was dissolved in a mixture solvent of propylene glycol monomethyl ether acetate (PGMEA), methylpyrrolidone, and gamma-butyrolactone in a ratio of 40:20:40 by volume, and the solution was filtered to prepare a hardmask composition.

[Formula 6a]

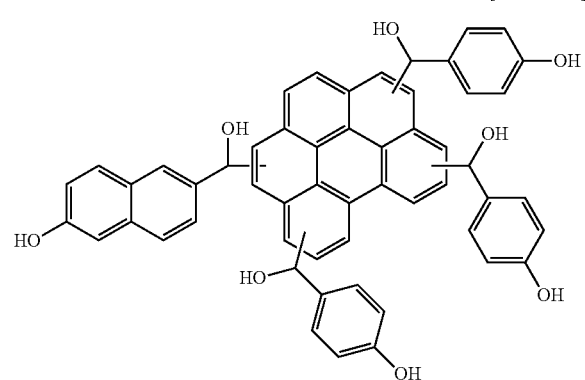

The hardmask composition obtained in the manner described above was coated on a silicon substrate having a silicon oxide layer pattern by using a spin-on coating method and then thermally treated at a temperature of about 400° C. for about 120 seconds to form a hardmask including spin-on-carbon (SOC).

An ArF photoresist (PR) was coated on the hardmask to a thickness of about 1700 Å and then pre-baked at a temperature of about 110° C. for about 60 seconds. The resultant was exposed to light by using a light exposing instrument (available from ASML, XT: 1400, and NA 0.93), post-baked at a temperature of about 110° C. for about 60 seconds, and then developed by using an 2.38 wt % aqueous solution of tetramethyl ammonium hydroxide (TMAH) to form a photoresist pattern.

Dry etching was performed using the photoresist pattern as a mask and a $CF_4/CHF_3$ mixture gas. The etching conditions included 20 mT of a chamber pressure, 1800 W of a RF power, a ratio of $C_4F_8$ to $CHF_3$ in 4:10 by volume, and an etching time of about 120 seconds.

$O_2$ ashing and wet stripping were performed on the hardmask and an organic material remaining after the dry etching to thereby obtain a desired silicon substrate having a silicon oxide layer pattern as a final pattern.

Comparative Example 2

A silicon substrate having a silicon oxide layer pattern was prepared as follows by using a hardmask including high-temperature amorphous carbon.

A carbon source ($C_3H_6$) was deposited on the silicon substrate having the silicon oxide pattern to form a hardmask including high-temperature amorphous carbon.

The deposition was performed by using a chemical vapor deposition method at a temperature of about 550° C., a pressure of about 0.01 mTorr to about 1 mTorr, an ion energy of about 50 eV to about 500 eV.

An ArF photoresist (PR) was coated on the hardmask to a thickness of about 1700 Å and then pre-baked at a temperature of about 110° C. for about 60 seconds. The resultant was exposed to light by using a light exposing instrument (available from ASML, XT: 1400, and NA 0.93), post-baked at a temperature of about 110° C. for about 60 seconds, and then developed by using an 2.38 wt % aqueous solution of tetramethyl ammonium hydroxide (TMAH) to form a photoresist pattern.

Dry etching was performed using the photoresist pattern as a mask and a $CF_4/CHF_3$ mixture gas. The etching conditions included 20 mT of a chamber pressure, 1800 W of a RF power, a ratio of $C_4F_8$ to $CHF_3$ in 4:10 by volume, and an etching time of about 120 seconds.

$O_2$ ashing and wet stripping were performed on the hardmask and an organic material remaining after the dry etching to thereby obtain a desired silicon substrate having a silicon oxide layer pattern as a final pattern.

Comparative Example 3

0.5 g of the OH-functionalized graphene quantum dots prepared according to Preparation Example 3 was dispersed in 1 L of water to obtain a hardmask composition. While spray-coating the hardmask composition on a silicon substrate having a silicon oxide layer pattern thereon, thermal treatment was performed at a temperature of 200° C. Subsequently, the resultant was baked at a temperature of 400° C. for 1 hour, and then heat-treated in a vacuum at a temperature of 600° C. for 1 hour to thereby form a hardmask having a thickness of about 200 nm and containing OH-functionalized graphene quantum dots.

An ArF photoresist (PR) was coated on the hardmask to a thickness of about 1700 Å and then pre-baked at a temperature of about 110° C. for about 60 seconds. The resultant was exposed to light by using a light exposing instrument (available from ASML, XT: 1400, and NA 0.93), post-baked at a temperature of about 110° C. for about 60 seconds, and then developed by using an 2.38 wt % aqueous solution of tetramethyl ammonium hydroxide (TMAH) to form a photoresist pattern.

Dry etching was performed using the photoresist pattern as a mask and a $CF_4/CHF_3$ mixture gas. The etching conditions included 20 mT of a chamber pressure, 1800 W of a RF power, a ratio of $C_4F_8$ to $CHF_3$ in 4:10 by volume, and an etching time of about 120 seconds.

$O_2$ ashing and wet stripping were performed on the hardmask and an organic material remaining after the dry etching to thereby obtain a desired silicon substrate having a silicon oxide layer pattern as a final pattern.

Evaluation Example 1

Solubility Test

A solubility test in cyclohexanone was performed on the OH-functionalized GQDs of Preparation Example 3 and the Diels-Alder reaction product of the OH-functionalized GQDs and dimethylacetylene dicarboxylate obtained in Manufacturing Example 1. The solubility test results are shown in Table 1.

TABLE 1

| Example | Solubility (wt %) |
| --- | --- |
| Preparation Example 3 (OH-functionalized GQDs) | less than 1 wt % |
| Manufacturing Example 1 (Diels-Alder reaction product) | 20 wt % |

Referring to Table 1, the Diels-Alder reaction product of Manufacturing Example 1 was found to have greatly improved solubility characteristics in cycylohexane, compared to the OH-functionalized graphene(GQDs) of Preparation Example 3.

Evaluation Example 2

Fourier-Transform Infrared (FTIR) Spectroscopy

The OH-functionalized GQDs obtained according to Preparation Example 3 and the Diels-Alder reaction product (FGQD) of the OH-functionalized GQDs and dimethylacetylene dicarboxylate obtained in Manufactured Example 1 were analyzed by Fourier-transform infrared (FTIR) spectroscopy. The results are shown in FIG. 4.

Figure 4:
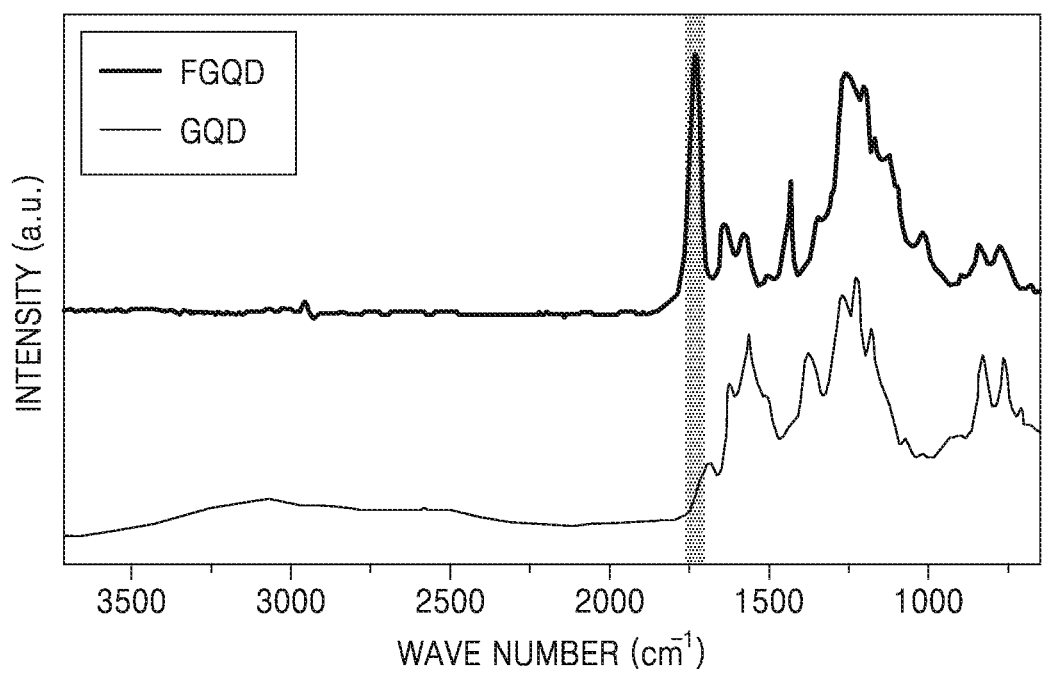
FIG. 4 illustrates Fourier-transform infrared (FTIR) spectra of OH-functionalized GQDs of Preparation Example 3 and a Diels-Alder reaction product (FGQD) according to Manufacture Example 1.

Referring to FIG. 4, the FGQD was found to have a reduced peak of free hydroxyl groups at the edge of the GQDs (at a wave number of about 2700 cm$^{-1}$ to about 3200 cm$^{-1}$), compared to the OH-functionalized GQDs of Preparation Example 3. A mixed ratio of sp$^3$ carbon to sp$^2$ carbon in the FGQD was higher than that of the OH-functionalized GQDs of Preparation Example 3 referring to information from a peak at a wave number of about 750 cm$^{-1}$ to about 1000 cm$^{-1}$.

Evaluation Example 3

X-Ray Photoelectron Spectroscopic (XPS) Analysis

Products from coating and drying the hard mask composition including the OH-functionalized GQDs obtained according to Preparation Example 3 and the hard mask composition including the Diels-Alder reaction product (FGQD) of the OH-functionalized GQDs and dimethylacetylene dicarboxylate obtained in Manufacturing Example 1 were analyzed by X-ray photoelectron spectroscopy (XPS) using a Quantum 2000 (available from Physical Electronics, Inc., Acceleration voltage: 0.5-15 keV, 300 W, Energy resolution: about 1.0 eV, and Sputter rate: 0.1 nm/min).

Figure 5A:
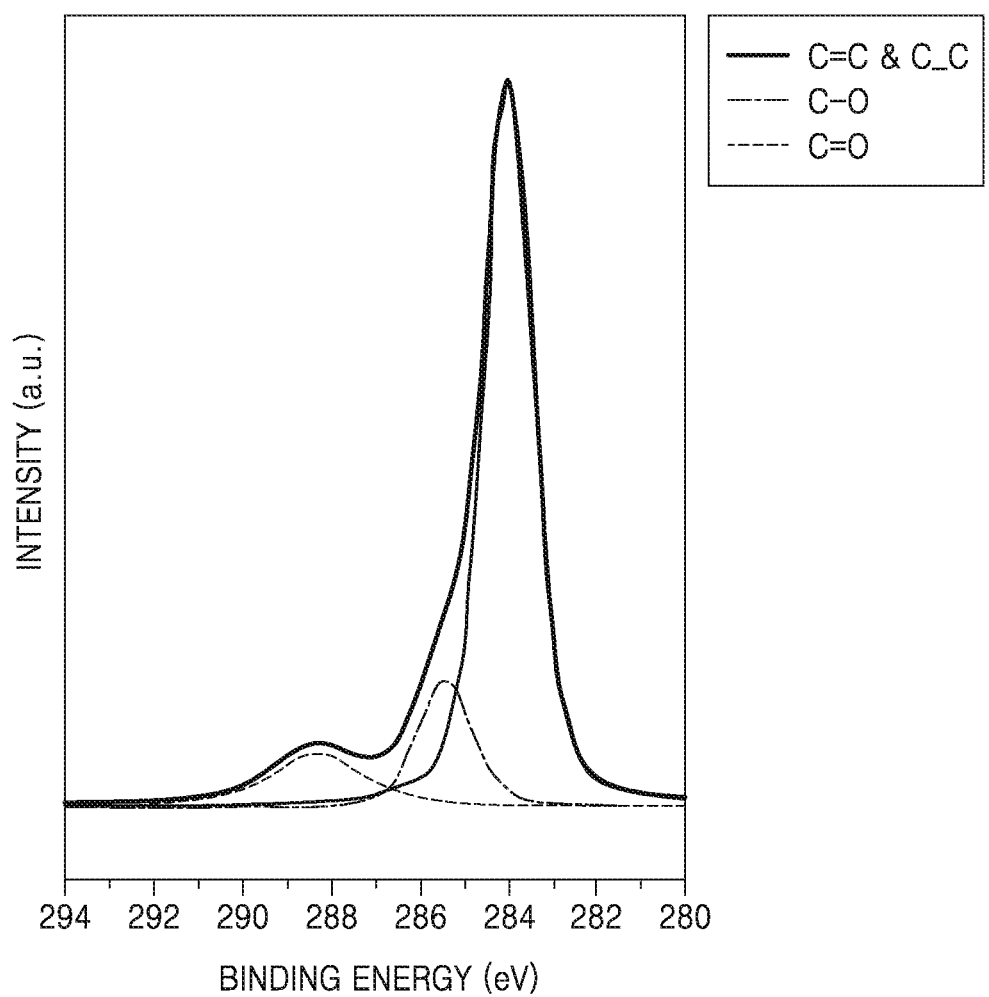
FIG. 5A illustrates X-ray photoelectron spectra (XPS) of a product from coating and drying the hardmask composition (composition A) including a Diels-Alder reaction product (FGQD) of the OH-functionalized GQDs and dimethylacetylene dicarboxylate according to Manufacturing Example 1.
Figure 5B:
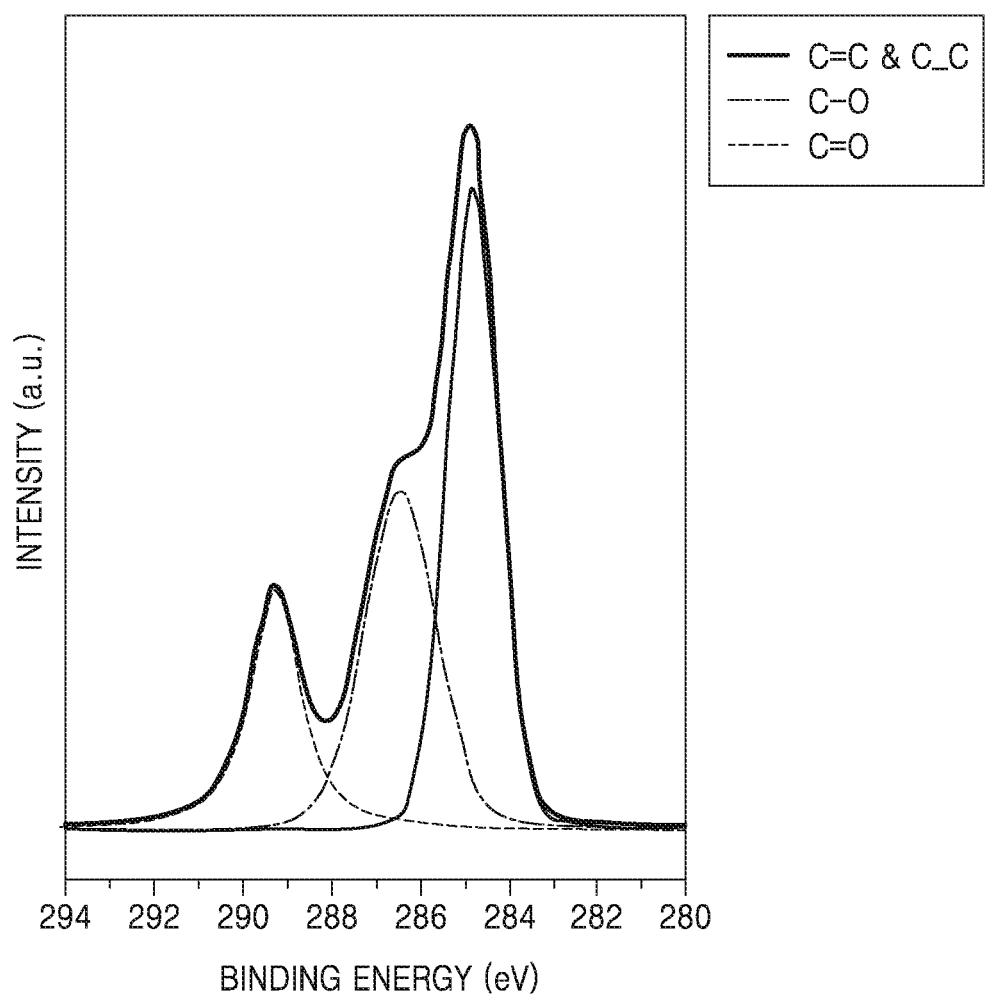
FIG. 5B illustrates XPS spectra of a product of coating and drying a hardmask composition including the OH-functionalized GQDs of Preparation Example 3 and a solvent.
Figure 5C:
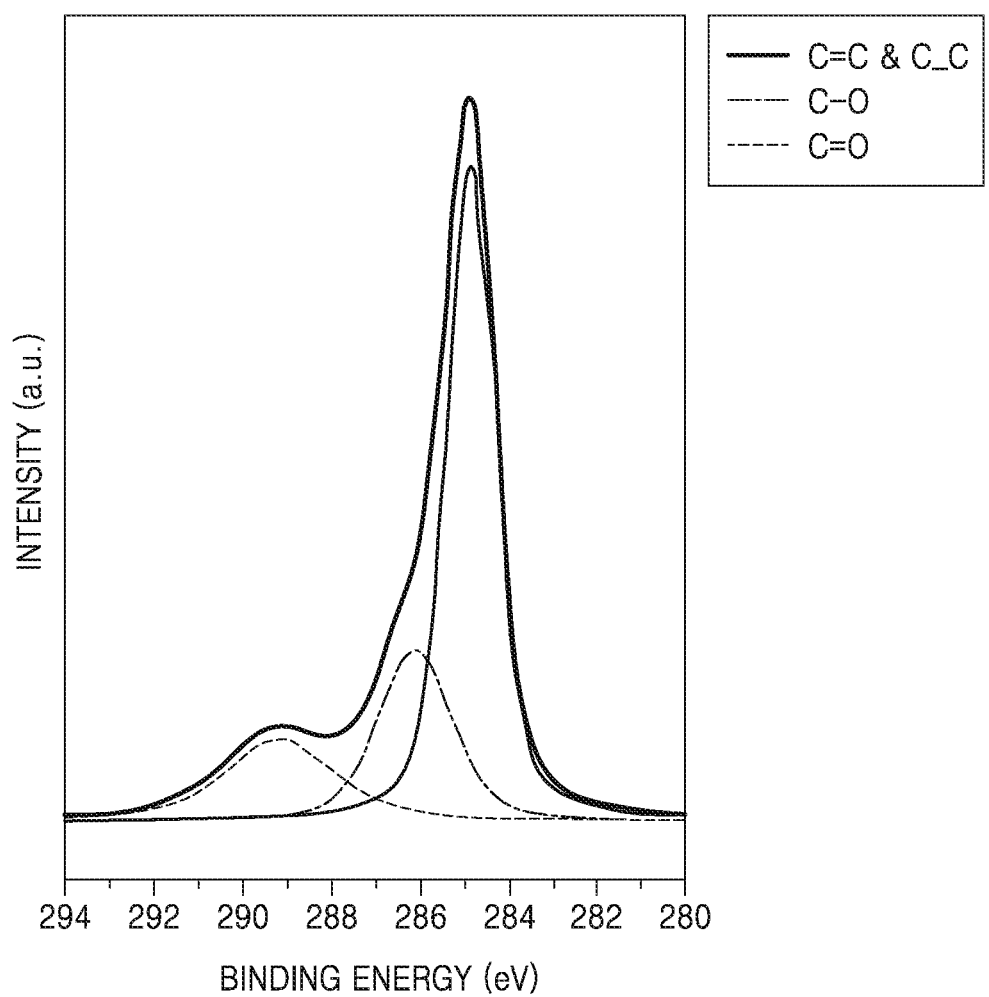
FIG. 5C illustrates XPS spectra of a product of further thermal treatment at about 400° C. of the product obtained by coating and drying the composition A.

The XPS results are shown in FIGS. 5A and 5B. The products obtained by thermally treating (baking) at about 400° C. the products from coating and drying the hard mask composition including the OH-functionalized GQDs of Preparation Example 3 and the hard mask composition including the Diels-Alder reaction product (FGQD) of Manufacturing Example 1 were analyzed by XPS. The results are shown in FIG. 5C FIG. 5A is an XPS result of the product from coating and drying the composition (composition A) including the Diels-Alder reaction product (FGQD) of the OH-functionalized GQD and dimethylacetylene dicarboxylate resulting from coating and drying the mask composition according to Manufacturing Example 1. FIG. 5B is a XPS result of a product of coating and drying the composition including the OH-functionalized GQDs of Preparation Example 3 and a solvent. FIG. 5C is an XPS result of a product of further thermal treatment at about 400° C. of the product obtained by coating and drying the composition A.

Referring to FIGS. 5A to 5C, the FGQD was found to have a larger content of sp$^3$ carbon, relative to the GQDs.

The contents of carbon, nitrogen, and oxygen were also analyzed by XPS. The results are shown in Table 2.

TABLE 2

| Example | | C (atom %) | N (atom %) | O (atom %) |
| --- | --- | --- | --- | --- |
| Preparation Example 3 | GQD (ref.) | 79.2 | 2.5 | 18.2 |
| | GQD (powder) | 71.0 | 2.6 | 25.7 |
| Manufacturing Example 1 | FGQD (as-dep) | 71.9 | 2.2 | 25.9 |
| | FGQD (bake) | 80.3 | 2.1 | 17.4 |

In Table 2, "GOD (ref.)" denotes the OH-functionalized GQDs of Preparation Example 3, "GOD (powder)" denotes the OH-functionalized GQDs in powder form, "FGQD (as-dep)" denotes the Diels-Alder reaction product of Manufacturing Example 1 as deposited immediately after the coating, and "FGQD (bake)" denotes a product of the thermal treatment (baking) of the Diels-Alder reaction product.

Referring to Table 2, the FGQD after the thermal treatment (baking) at about 400° C. was found to have a reduced oxygen content by about 4.26% and an increased carbon content by about 1.26%, relative to the GQD (ref.) of Preparation Example 3. By using the FGQDs having such a reduced oxygen content and increased carbon content, a hardmask having improved stability and etch selectivity was obtained.

Evaluation Example 4

Thermogravimetric Analysis (TGA)

The OH-functionalized GQDs of Preparation Example 3 and the Diels-Alder reaction product (FGQD) of Manufacturing Example 1 were analyzed by thermogravimetric analysis (TGA) using a TA Instruments SDT 2010 TGA/DSC1 (available from METTLER TOLEDO) (in a temperature range of about 25° C. to about 1600° C.). The TGA results are shown in FIG. 6.

Figure 6:
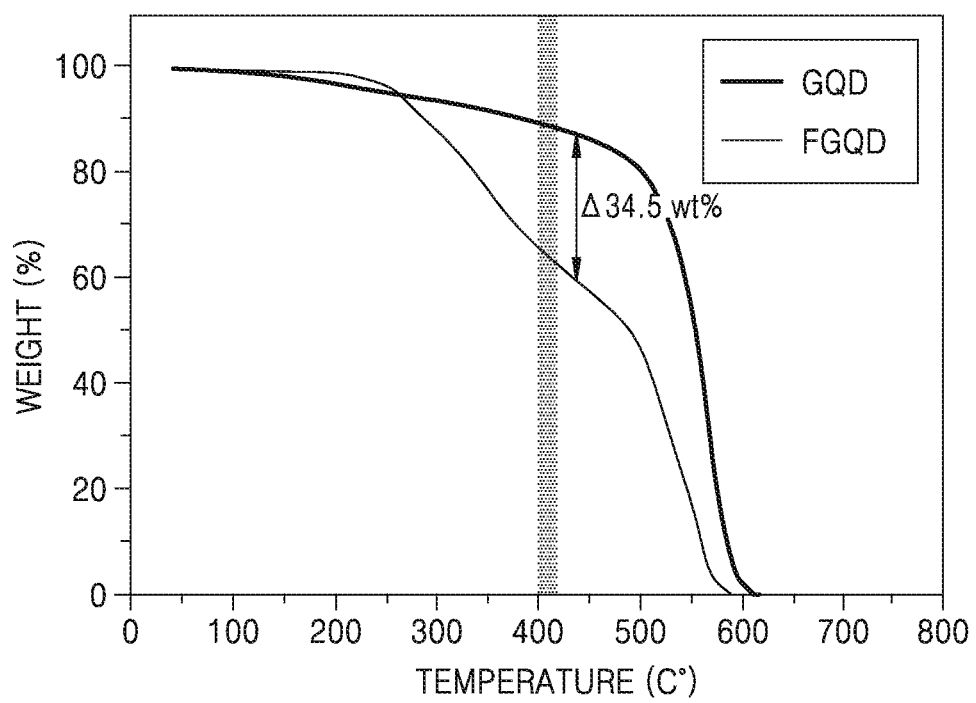
FIG. 6 illustrates results of thermogravimetric analysis (TGA) of the OH-functionalized GQDs of Preparation Example 3 and the Diels-Alder reaction product (FGQD) obtained according to Manufacturing Example 1 using the hardmask composition prepared according to Example 1.

Referring to FIG. 6, the Diels-Alder reaction product (FGQD) was found to have a weight reduction by about 34.5 wt % at a temperature of about 400° C., relative to the GQDs of Preparation Example 3. This result indicates that the amount of functional groups in the Diels-Alder reaction product (FGQD) which contribute the solubility of GQDs in a process solvent was about 34.5 wt %.

Evaluation Example 5

Rutherford Backscattering Spectroscopy (RBS) and Density Analysis

The hardmasks according to Manufacturing Example 1, Comparative Example 2, and Comparative Example 3 were evaluated by Rutherford backscattering spectrometry. The RBS results are shown in Table 3.

The densities of the hardmasks according to Manufacturing Example 1 and Comparative Examples 1 and 3 were evaluated. The results are also shown in Table 3.

TABLE 3

| Example | C (atom %) | N (atom %) | O (atom %) | H (atom %) | Density (g/cm$^3$) |
|---|---|---|---|---|---|
| Comparative Example2 (ACL) | 78.1 | 1.8 | 3.2 | 16.9 | 1.54 |
| Manufacturing Example 1 FGQD (as-dep) | 61.2 | 2.5 | 7.4 | 28.9 | 0.87 |
| Manufacturing Example 1 FGQD (bake) | 65.0 | 3.7 | 10.7 | 20.6 | 1.34 |
| Comparative Example3 | 68.0 | 3.0 | 9.3 | 19.7 | 1.25 |
|  | 68.5 | 2.1 | 8.6 | 20.9 | 1.34 |

Referring to Table 3, it was found that the functional groups bound to the GQDs were removed from the GQDs under general spin-on-hardmask process conditions (i.e., the thermal treatment at about 400° C. for 2 minutes).

Evaluation Example 6

Transmittance

Transmittances of the hardmasks according to Manufacturing Example 1 and Comparative Examples 1 to 3 were measured at an exposure wavelength of about 633 nm.

As a result of the measurement, the hardmask patterns of Manufacturing Example 1 was found to have an improved transmittance of about 99% or less, relative to the hardmask patterns of Comparative Examples 1 to 3. When using such a hardmask having an improved transmittance, a hardmask pattern and an alignment mark for patterning a target etching layer may be easily detected, so that the target etching layer may be patterned into a fine and compact pattern.

Evaluation Example 7

Etching Resistance

Thickness differences of the hardmasks and the silicon oxide layers according to Manufacturing Example 1 and Comparative Examples 1 to 3 between before and after etching were evaluated. Etching resistances of the hardmasks were evaluated based on the etch rate and etching selectivity thereof calculated using Equations 1 and 2, respectively.

Etch rate=(Initial thin film thickness−Thin film thickness after etching)/Etching time(sec)   [Equation 1]

Etch selectivity=(Silicon oxide layer's thickness before etching−Silicon oxide layer's thickness after etching)/(Hardmask's thickness before etching−Hardmask's thickness after etching)× 100.   [Equation 2]

As a result of evaluating etching resistance, the hardmask according to Manufacturing Example 1 was found to have a lower etch rate and an increased etching selectivity relative to the hardmasks according to Comparative Examples 1 to 3. This result indicates that the hardmask composition of Example 1 had improved etching resistance relative to the hardmask compositions used in Comparative Examples 1 to 3.

As described above, according to the one or more embodiments, when using a hardmask composition according to the above-described embodiments using graphene quantum dots having good solubility characteristics in a semiconductor process solvent, a hardmask having improved stability may be manufactured. The hardmask may also have improved etching resistance and improved mechanical strength, and thus may be easily removed after an etching process, relative to a hardmask using a common polymer. When the hardmask according to embodiments is used, a finer pattern having improved uniformity may be formed, and efficiency of a semiconductor process may also be improved.

FIGS. 7A to 7E are cross-sectional views for explaining a method of forming an electronic device using a hardmask composition according to some example embodiments.

Figure 7A:
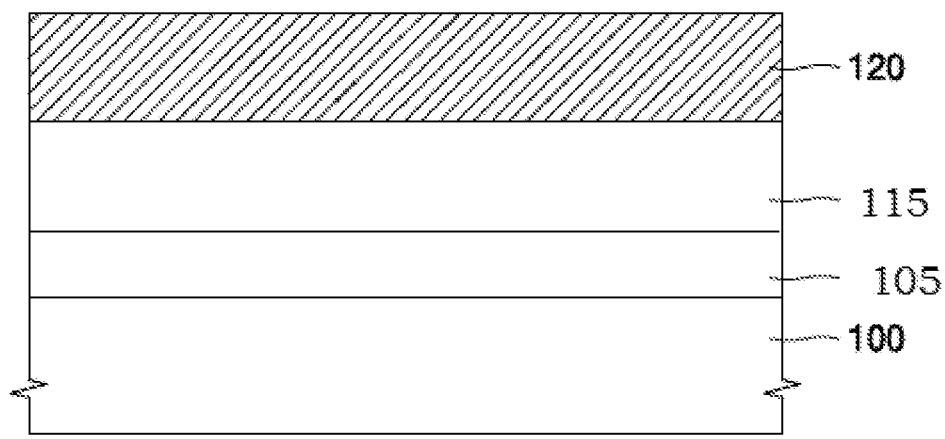

Referring to FIG. 7A, a gate dielectric 105 (e.g., silicon oxide) may be formed on a substrate 100. The substrate 100 may be formed of any one of the materials of the substrates 10 and 20 described above with reference to FIGS. 2A to 2E and 3A to 3D. A gate layer 115 (e.g., doped polysilicon) may be formed on the gate dielectric 105. A hardmask composition according to any of the above-described embodiments may be provided on the gate layer 115 in order to form a hardmask layer 120.

Figure 7B:
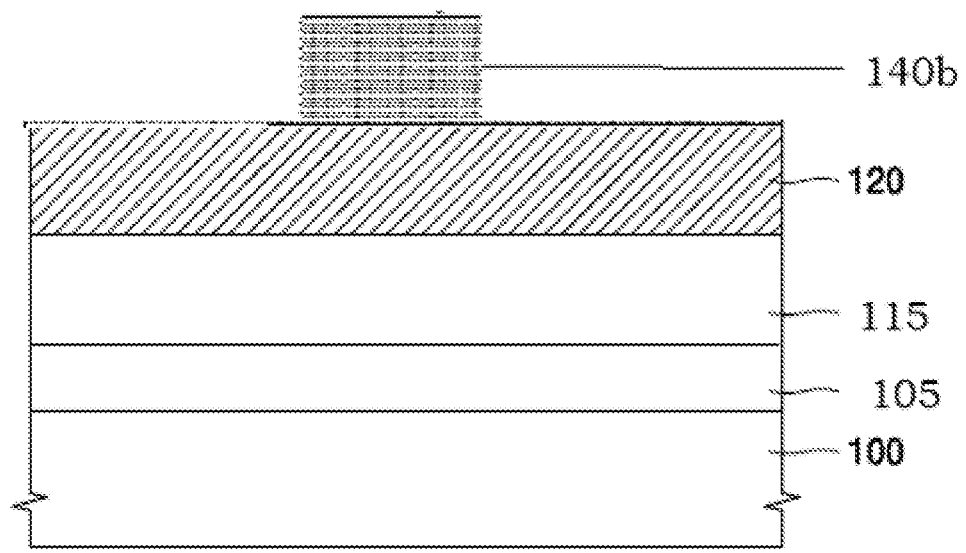

Referring to FIG. 7B, a photoresist pattern 140b may be formed on the hardmask layer 120.

Figure 7C:
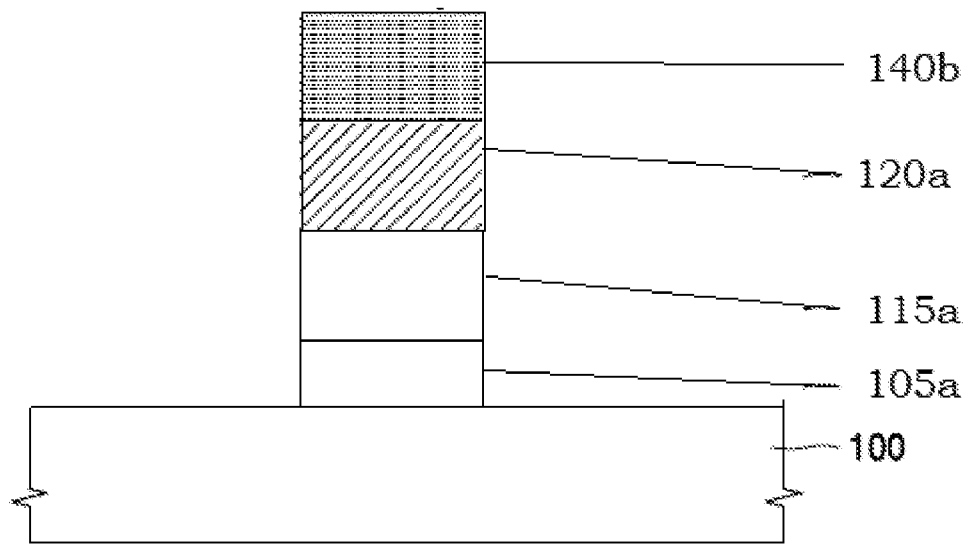

Referring to FIG. 7C, the gate layer 115 and the gate dielectric 105 may be etched to form a gate electrode pattern 115a and a gate dielectric pattern 105a. Although not illustrated in FIGS. 7B and 7C, in some embodiments, an anti-reflection layer like the anti-reflection layer 30 in FIG. 3A may be formed on the hardmask layer 120 before forming the photoresist pattern 140b on the hardmask layer 120 and the etching process described in FIG. 7C may form an anti-reflection pattern 30a on the gate electrode pattern 115a in some embodiments.

Figure 7D:
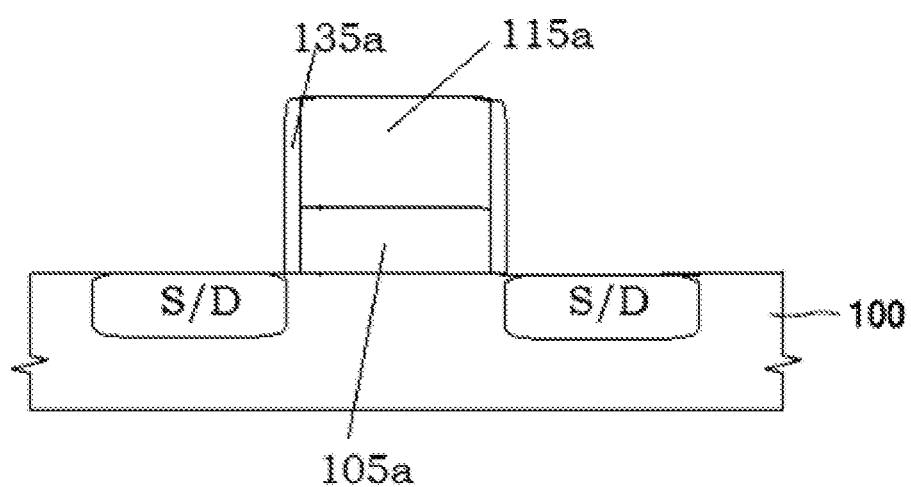

Referring to FIG. 7D, a spacer layer may be formed over the gate electrode pattern 115a and the gate dielectric pattern 105a. The spacer layer may be formed using a deposition process (e.g., CVD). The spacer layer may be etched to form spacers 135a (e.g., silicon nitride) on sidewalls of the gate electrode pattern 115a and the gate dielectric pattern 105a. After forming the spacers 135a, ions may be implanted into the substrate 100 to form source/drain impurity regions S/D.

Referring to FIG. 7E, an interlayer insulating layer 160 (e.g., oxide) may be formed on the substrate 100 to cover the gate electrode pattern 115a, gate dielectric pattern 105a, and spacers 135a. Then, electrical contacts 170a, 170b, and 170c may be formed in the interlayer insulating layer 160 to connect to the gate electrode 115a and the S/D regions. The electrical contacts may be formed of a conductive material (e.g., metal). Although not illustrated, a barrier layer may be formed between sidewalls of the interlayer insulating layer 160 and the electrical contacts 170a, 170b, and 170c. While FIGS. 7A to 7E illustrate an example of forming a transistor, inventive concepts are not limited thereto. Hardmask compositions according one or more embodiments may be used in a patterning process to form other types of electronic devices.

It should be understood that embodiments described herein should be considered in a descriptive sense only and not for purposes of limitation. Descriptions of features or aspects within each embodiment should typically be considered as available for other similar features or aspects in other embodiments.

While one or more embodiments have been described with reference to the figures, it will be understood by those of ordinary skill in the art that various changes in form and details may be made therein without departing from the spirit and scope as defined by the following claims.

What is claimed is:

1. A hardmask composition comprising:
   one of,
   a mixture of graphene quantum dots and at least one selected from a diene and a dienophile,
   a Diels-Alder reaction product of the graphene quantum dots and the at least one selected from a diene and a dienophile,
   a thermal treatment product of the Diels-Alder reaction product of the graphene quantum dots and the at least one selected from a diene and a dienophile, or
   a combination thereof; and
   a polar nonaqueous organic solvent.

2. The hardmask composition of claim 1, wherein
   the graphene quantum dots include at an end thereof at least one first functional group, and
   the at least one first functional group is selected from the group consisting of a hydroxyl group, a carbonyl group, a carboxyl group, an epoxy group, and an amine group.

3. The hardmask composition of claim 1, wherein the diene and the dienophile include a second functional group that is the same as or similar to that of the polar nonaqueous organic solvent.

4. The hardmask composition of claim 3, wherein the second functional group is at least one selected from the group consisting of a C1-C20 alkenylene group including a carboxyl group, an organic group including a carbonyl group, an organic group including —COOR (wherein R is a C1-C20 alkyl group or a C2-C20 alkenyl group), a hydrogenated C1-C10 cyanoalkylene group, a hydrogenated C4-C20 heterocyclic group, a hydrogenated C2-C20 alkenyl group, and a hydrogenated C4-C20 condensed arylene group.

5. The hardmask composition of claim 1, wherein the polar nonaqueous organic solvent is at least one selected from propylene glycol monomethylether acetate (PGMEA), propylene glycol monomethyl ether (PGME), cyclohexanone, and ethyl lactate.

6. The hardmask composition of claim 1, wherein the at least one selected from a diene and a dienophile is at least one selected from the group consisting of dimethylacetylene dicarboxylate, acrolein, maleic acid ester, acrylonitrile, fumaric acid ester, maleic anhydride, tetracyanoethylene, benzoquinone, a group represented by Formula 1, and a group represented by Formula 2.

[Formula 1]

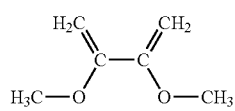

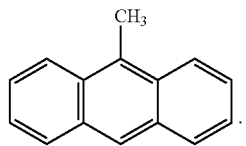

[Formula 2]

7. The hardmask composition of claim 1, wherein at least one of an amount of the at least one selected from a diene and a dienophile is about 100 parts by weights or higher based on 100 parts by weight of the graphene quantum dots.

8. The hardmask composition of claim 1, wherein the graphene quantum dots have a size of about 1 nm to about 50 nm.

9. The hardmask composition of claim 1, wherein the Diels-Alder reaction product of the graphene quantum dots and the at least one selected from a diene and a dienophile has a structure in which the graphene quantum dots are bound to one or more structures represented by Formula 3:

[Formula 3]

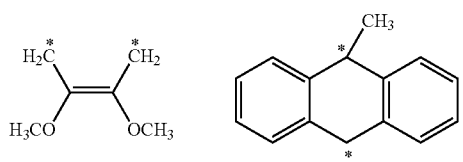

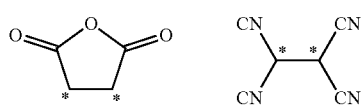

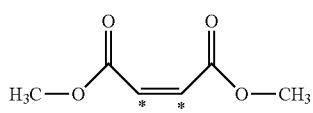

wherein, in Formula 3, * indicates a binding site to the graphene quantum dots.

10. The hardmask composition of claim 1, wherein the Diels-Alder reaction product of the graphene quantum dots and the at least one selected from a diene and a dienophile is has a structure represented by one or more groups in Formula 4 to Formula 8,

[Formula 4]

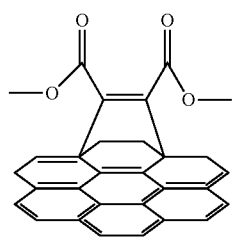

[Formula 5]

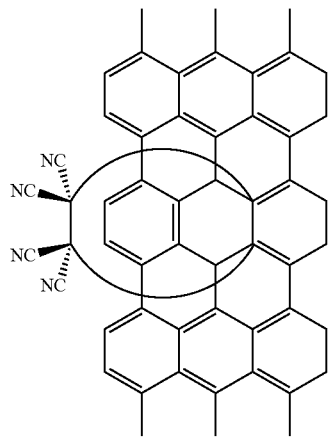

[Formula 6]

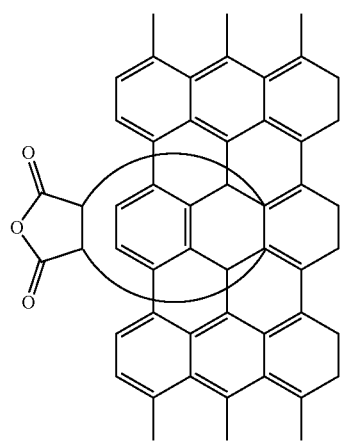

[Formula 7]

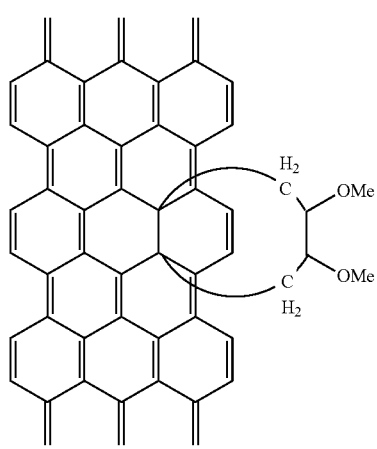

[Formula 8]

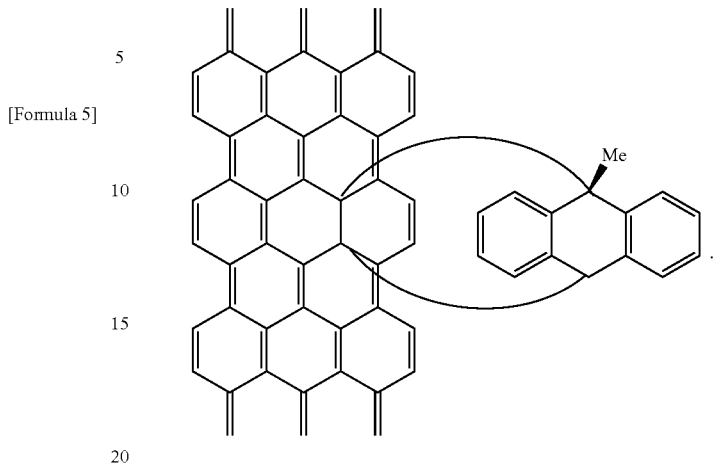

11. The hardmask composition of claim 1, further comprising:
an additional organic solvent, wherein
the additional organic solvent is selected from the group consisting of methanol, isopropanol, ethanol, N,N-dimethylformamide, N-methylpyrrolidone, dichloroethane, dichlorobenzene, N,N-dimethylsulfoxide, aniline, propylene glycol, propylene glycol diacetate, 3-methoxy1,2-propanediol, diethylene glycol, acetylacetone, cyclohexanone, propylene glycol monomethyl ether acetate, γ-butyrolactone, dichloroethane, dichlorobenzene, nitromethane, tetrahydrofuran, nitrobenzene, butyl nitrite, methylcellosolve, ethylcellosolve, diethyl ether, diethylene glycol methyl ether, diethylene glycol ethyl ether, dipropylene glycol methyl ether, toluene, xylene, hexane, methyl ethyl ketone, methyl isopropylbutyl ketone, hydroxymethyl cellulose, heptane, and water, or a mixture thereof.

12. The hardmask composition of claim 1, further comprising:
at least one of a first material, a second material, or combination thereof, wherein
the first material selected from an aromatic ring-containing monomer and a polymer containing a repeating unit including an aromatic ring-containing monomer, and
the second material is selected from the group consisting of a hexagonal boron nitride derivative, a chalcogenide material, a hexagonal boron nitride derivative precursor, and a metal chalcogenide material precursor, or a combination thereof.

13. A method of forming a pattern, comprising:
forming a target etching layer on a substrate;
forming a hardmask on the target etching layer, the hardmask including a product of coating the hardmask composition of claim 1 onto the target etching layer and thermally treating the hardmask composition;
forming a photoresist layer on the hardmask;
forming a hardmask pattern using the photoresist layer as an etch mask, the hardmask pattern including the product of coating and thermally treating the hardmask composition; and
etching the target etching layer using the hardmask pattern as an etch mask.

14. The method of claim 13, wherein the hardmask composition is prepared by mixing the polar nonaqueous organic solvent and the mixture of the graphene quantum dots and the at least one selected from a diene and a dienophile.

15. The method of claim 14, wherein the graphene quantum dots include OH-functionalized graphene quantum dots, COOH-functionalized graphene quantum dots, or a graphene quantum dot precursor.

16. A hardmask comprising:
a product resulting from coating and thermally treating the hardmask composition of claim 1.

17. The hardmask of claim 16, wherein the product resulting from coating and thermally treating the hardmask composition includes the thermal treatment product of a Diels-Alder reaction product of the graphene quantum dots and the at least one selected from a diene and a dienophile.

18. The hardmask of claim 16, wherein an oxygen content of the graphene quantum dots of the hardmask is about 3% or more lower than an oxygen content of the graphene quantum dots as a starting material, as analyzed by X-ray photoelectron spectroscopy.

19. The hardmask of claim 16, wherein the hardmask has a reduced intensity of a peak corresponding to free hydroxyl groups at a wave number of about 2700 $cm^{-1}$ to 3200 $cm^{-1}$, relative to a peak corresponding to free hydroxyl groups in the graphene quantum dots used as a starting material, and the hardmask has an increased mixed ratio of $sp^3$ carbon to $sp^2$ carbon, relative to a corresponding peak of the graphene quantum dots used as a starting material, as analyzed by infrared (IR) spectroscopy.

20. The hardmask of claim 16, wherein the hardmask has an increased peak intensity ratio ($I_{sp3}/I_{sp2}$) of an $sp^3$ carbon peak to an $sp^2$ carbon peak, relative to a peak intensity ratio ($I_{sp3}/I_{sp2}$) of an $sp^3$ carbon peak to an $sp^2$ carbon peak in graphene quantum dots used as a starting material, as analyzed by X-ray photoelectron spectroscopy (XPS).

* * * * *